United States Patent
Chen et al.

(10) Patent No.: US 6,677,452 B1
(45) Date of Patent: Jan. 13, 2004

(54) PYRIDINE CARBOXAMIDE OR SULFONAMIDE DERIVATIVES AND COMBINATORIAL LIBRARIES THEREOF

(75) Inventors: Yuewu Chen, San Diego, CA (US); Hengyuan Lang, San Diego, CA (US); Yazhong Pei, Aliso Viejo, CA (US)

(73) Assignee: Lion Bioscience AG (DE)

( * ) Notice: Subject to any disclaimer, the term of this patent is extended or adjusted under 35 U.S.C. 154(b) by 0 days.

(21) Appl. No.: 09/410,142

(22) Filed: Sep. 30, 1999

(51) Int. Cl.[7] .................... C07D 401/04; C07D 401/14; C07D 213/72
(52) U.S. Cl. ................. 544/365; 546/276.4; 546/275.7; 546/268.1; 546/262; 546/256; 546/193; 546/309; 546/297; 544/360
(58) Field of Search ........................ 546/276.4, 275.7, 546/268.1, 262, 256, 193, 309, 297; 544/365, 360

(56) References Cited

U.S. PATENT DOCUMENTS 3,615,504 A 10/1971 Monbaliu et al.

FOREIGN PATENT DOCUMENTS

| EP | 0 429 372 A1 | 5/1991 |
| WO | WO 97/28128 | 8/1997 |
| WO | WO 98/00134 | 8/1998 |

OTHER PUBLICATIONS

Gordon et al., "Applications of Combinatorial Technologies to Drug Discovery," *J. Med. Chem.*, 37(10) : 1385–1401 (1994).
Romero et al., "Discovery, Synthesis, and Bioactivity of Bis(heteroaryl) piperazines," *J. Med. Chem.*, 37:999–1014 (1994).
Chen et al., "Solid Phase Synthesis of 2,4–Disubstituted Pyridine and Tetrahydropyridine Derivatives: Resin Activation/Capture Approach/REACAP Technology," *Tetr. Lett.*, 39:3401–3404 (1998).
Cotterill et al., "Microwave Assisted Combinatorial Chemistry Synthesis of Substituted Pyridines," *Tetr. Lett.*, 39:1117–1120 (1998).
Gordeev et al., "Approaches to Combinatorial Synthesis of Heterocycles: Solid Phase Synthesis of Pyridines and Pyrido [2,3–d] pyrimidines," *Tetr. Lett.*, 37:4643–4646 (1996).
Katritzky et al., "Benzotriazole–Assisted Preparations of 2–(Substituted amino) pyridines and Pyrid–2–ones," *J. Org. Chem.*, 62:6210–6214 (1997).
Lago et al., "Solid Phase Synthesis of a 1,3,5,–Trisubstituted Pyridinium Salt Library," *Tetr. Lett.*, 39:3885–3888 (1998).
Mohan et al., "Solid–Phase Synthesis of N–Substituted Amidinophenoxy Pyridines As Factor XA Inhibitors," *Bioorg. & Med. Chem. Lett.*, 8:1877–1882 (1998).
Nitta et al., "On the Reaction of (Vinylimino) phosphoranes. Part 17.) Preparation of N–Vinylcarbodiimides and Their [4+2] Cycloaddition with Several Dienophiles to Give Pyridine Ring System," *Bull. Chem. Soc. Jpn.*, 64:1325–1331 (1991).
Ngu and Patel, Preparation of Acid–labile Resins with Halide Linkers and their Utility in Solid Phase Organic Synthesis, *Tetr. Lett.*, 38:973–976 (1997).
Pabst et al., "A New and Simple 'LEGO' System for the Synthesis of Branched Oligopyridines," *Tetr. Lett.*, 39:6691–6694 (1998).
Power et al., "Automated Parallel Synthesis of Chalcone–Based Screening Libraries," *Tetrahedron*, 54:4085–4096 (1998).
Tadesse et al., "Solid–Phase Synthesis of Highly Functionalized 2,2'–Bipyridines," *J. Comb. Chem.*, 1:184–187 (1999).

*Primary Examiner*—Charanjit S. Aulakh
(74) *Attorney, Agent, or Firm*—Law Office of David Spolter

(57) ABSTRACT

The present invention relates to novel pyridine carboxamide or sulfonamide derivative compounds of the following formula:

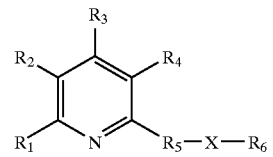

wherein $R_1$ to $R_6$ have the meanings provided herein. The invention further relates to combinatorial libraries containing two or more such compounds, as well as methods of preparing pyridine carboxamide or sulfonamide derivative compounds.

24 Claims, 1 Drawing Sheet

PYRIDINE CARBOXAMIDE OR SULFONAMIDE DERIVATIVES AND COMBINATORIAL LIBRARIES THEREOF

FIELD OF THE INVENTION

The present invention relates generally to the synthesis of compounds comprising heterocyclic rings. In one specific embodiment, the invention provides novel pyridine carboxamide or sulfonamide derivative compounds as well as novel combinatorial libraries comprised of such compounds.

BACKGROUND INFORMATION

The process of discovering new therapeutically active compounds for a given indication involves the screening of all compounds from available compound collections. From the compounds tested, one or more structures is selected as a promising lead. A large number of related analogs are then synthesized in order to develop a structure-activity relationship and select one or more optimal compounds. With traditional "one-at-a-time" synthesis and biological testing of analogs, this optimization process is long and labor intensive. Adding significant numbers of new structures to the compound collections used in the initial screening step of the discovery and optimization process cannot be accomplished with traditional "one-at-a-time" synthesis methods, except over a time frame of years or even decades. Faster methods are needed that allow for the preparation of up to thousands of related compounds in a matter of days or a few weeks. This need is particularly evident when it comes to synthesizing more complex compounds, such as pyridine carboxamide or sulfonamide derivative compounds.

Combinatorial chemical methods have been extended to pyridine derivative compounds, as described, for example, in Mohan et al, *Bioorg. & Med. Chem. Lett.*, 8:1877–1882 (1998); Tadesse et al, *J. Comb. Chem.*, 1:184–187 (1999); Gordeev et al, *Tetr. Lett.*, 37:4643–4646 (1996); Chen et al, *Tetr. Lett.*, 39:3401–3404 (1998); Coterill et al., *Tetr. Lett.*, 39:1117–1120 (1998); Lago et al., *Tetr. Lett.*, 39:3885–3888 (1998); and Powers et al., *Tetrahedron*, 54:4085–4096 (1998). However, the pyridine derivative libraries to date contain compounds of limited diversity and complexity.

A need therefore exists to develop more complex libraries based on heterocyclic medicinal compounds which would need less time and effort in the synthesis and testing required to bring an organic pharmaceutical product to fruition. In short, improved methods for generating therapeutically useful heterocyclic compounds, such as pyridine carboxamide or sulfonamide derivatives, are desired.

Pyridine derivative compounds have been the subject of investigation in a number of different biological areas. For example, pyridine derivatives have been proposed or used as anticoagulents (see Mohan et al., supra), antihistamines, antiseptics, antiarrhythmics and antirheumatics (see, Gordeev et al, supra). And pyridine carboxamide derivatives have fibirnogen receptor antagonists (see Duggan et al., WO 9800134 A1 (1998)).

Pyridine derivatives have also been the subject of serial chemical synthesis. See, for example, Katritzky et al., *J. Org. Chem.*, 62:6210–6214 (1997); Nitta et al., *Bull. Chem. Soc. Jpn.*, 64:1325–1331 (1991); and Pabst et al., *Tetr. Lett.*, 39:6691–6694 (1998). Pyridine carboxamide derivatives have also been the subject of serial chemical synthesis. See Lago et al., supra. However, more complex pyridine carboxamide or sulfonamide derivatives, especially those amino substituted at the 2 position, have been difficult to attain.

This invention satisfies this need and provides related advantages as well. The present invention overcomes the known limitations to classical serial organic synthesis of pyridine carboxamide or sulfonamide derivatives, for example, as well as the shortcomings of combinatorial chemistry related to pyridine carboxamide or sulfonamide derivatives. The present invention allows for rapid generation of large diverse libraries of complex pyridine carboxamide or sulfonamide derivatives as discrete molecules. The present invention can utilize a readily available pool of building blocks that can be incorporated into the various regions of the molecule. Furthermore, the method of making the present invention allows for the use of building blocks that contain a wide range of diverse functionality. Such building blocks can provide combinatorial libraries that consist of large numbers as well as combinatorial libraries that are extremely diverse with respect to the functionality contained within those libraries. The present invention combines the techniques of solid-phase synthesis of pyridine carboxamide or sulfonamide derivatives and the general techniques of synthesis of combinatorial libraries to prepare highly diverse new pyridine carboxamide or sulfonamide derivative compounds.

SUMMARY OF THE INVENTION

The present invention relates to novel pyridine carboxamide or sulfonamide derivative compounds of the following formula:

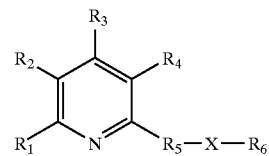

wherein $R_1$ to $R_6$ have the meanings provided herein.

The invention further relates to combinatorial libraries containing two or more such compounds, as well as methods of preparing pyridine carboxamide or sulfonamide derivative compounds.

BRIEF DESCRIPTION OF THE DRAWING

FIG. 1 shows the reaction scheme for the combinatorial synthesis of pyridine carboxamide derivative compounds.

DETAILED DESCRIPTION OF THE INVENTION

Figure 1:
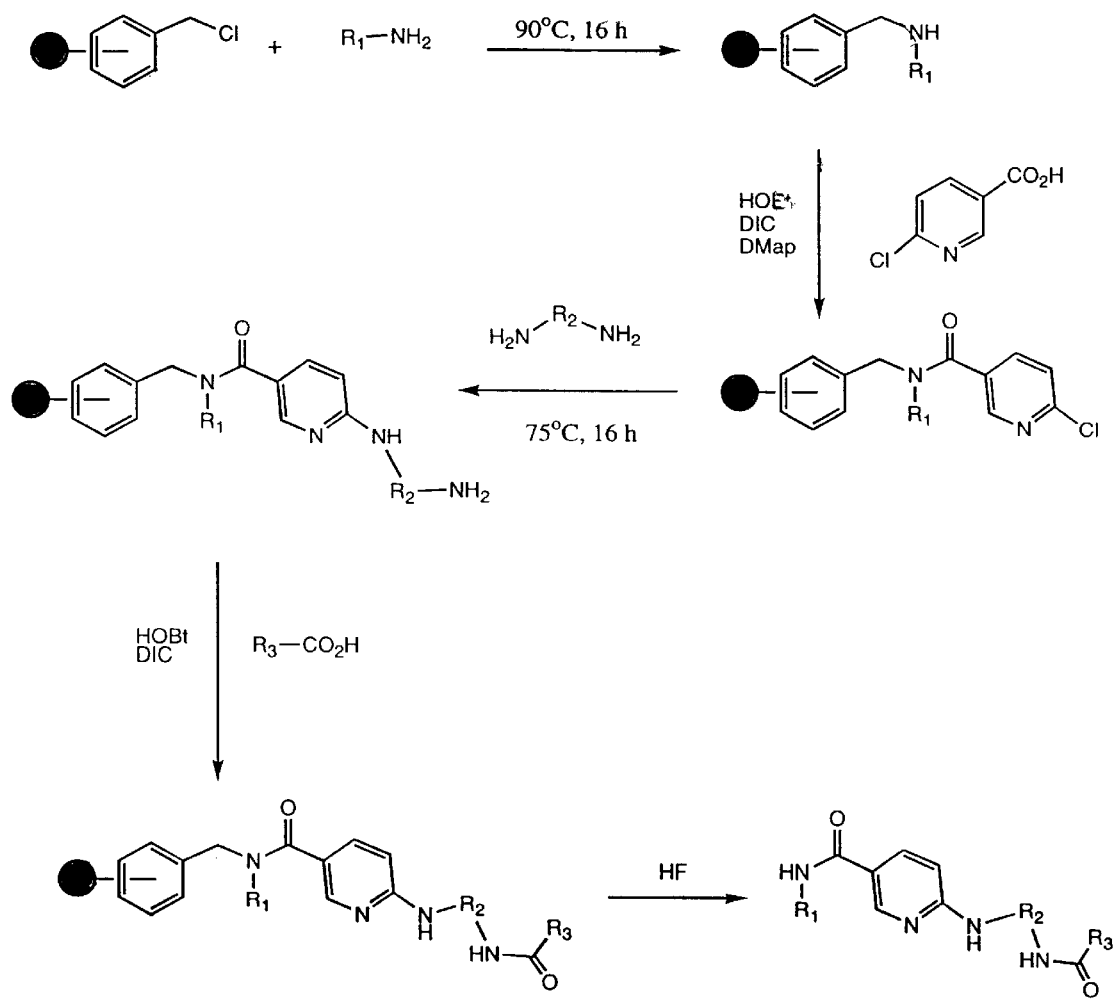
In FIG. 1, described below, as well as the examples, $R_1$ corresponds to $R_7$ of the claimed invention; —NH—$R_2$—NH— corresponds to $R_5$ of the claimed invention; and $R_3$ corresponds to $R_6$ of the claimed invention.

The present invention provides compounds and combinatorial libraries of compounds of the formula:

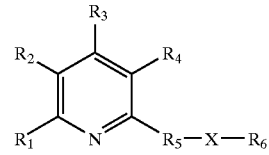

wherein:

X is a carbonyl group (—C(O)—) or a sulfonyl group (—S(O$_2$)—);

one of $R_1$, $R_2$, $R_3$ and $R_4$ is the formula —X—N—$R_7R_8$, wherein X is a carbonyl group (—C(O)—) or a sulfonyl group (—S(O$_2$)—);

$R_7$ is a hydrogen atom, $C_1$ to $C_{12}$ alkyl, $C_1$ to $C_{12}$ substituted alkyl, phenyl, substituted phenyl, heterocycle, substituted heterocycle, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, $C_2$ to $C_{12}$ alkenyl, $C_2$ to $C_{12}$ substituted alkenyl, $C_7$ to $C_{18}$ phenylalkyl, $C_7$ to $C_{18}$ substituted phenylalkyl, $C_1$ to $C_{12}$ heterocycloalkyl or $C_1$ to $C_{12}$ substituted heterocycloalkyl; and $R_8$ is a hydrogen atom, $C_1$ to $C_{12}$ alkyl, $C_1$ to $C_{12}$ substituted alkyl, non-aromatic heterocycle, non-aromatic substituted heterocycle, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, $C_2$ to $C_{12}$ alkenyl, $C_2$ to $C_{12}$ substituted alkenyl, $C_7$ to $C_{18}$ phenylalkyl, $C_7$ to $C_{18}$ substituted phenylalkyl, $C_1$ to $C_{12}$ heterocycloalkyl or $C_1$ to $C_{12}$ substituted heterocycloalkyl;

the remaining $R_1$, $R_2$, $R_3$ and $R_4$ are, independently, a hydrogen atom, hydroxy, protected hydroxy, nitro, cyano, $C_1$ to $C_{12}$ alkyl, $C_2$ to $C_{12}$ alkenyl, $C_2$ to $C_{12}$ alkynyl, $C_1$ to $C_{12}$ substituted alkyl, $C_2$ to $C_{12}$ substituted alkenyl, $C_2$ to $C_{12}$ substituted alkynyl, $C_1$ to $C_{12}$ alkoxy, $C_1$ to $C_{12}$ substituted alkoxy, $C_1$ to $C_{12}$ acyloxy, $C_1$ to $C_{12}$ acyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, heterocyclic ring, substituted heterocyclic ring, $C_7$ to $C_{18}$ phenylalkyl, $C_7$ to $C_{18}$ substituted phenylalkyl, $C_1$ to $C_{12}$ heterocycloalkyl, $C_1$ to $C_{12}$ substituted heterocycloalkyl, phenyl, substituted phenyl, naphthyl, substituted naphthyl, Cyclic $C_3$ to $C_7$ alkylene, substituted cyclic $C_3$ to $C_7$ alkylene, cyclic $C_2$ to $C_7$ heteroalkylene, substituted cyclic $C_2$ to $C_7$ heteroalkylene, carboxy, protected carboxy, hydroxymethyl, protected hydroxymethyl, protected amino, (monosubstituted) amino, protected (monosubstituted) amino, (disubstituted)amino, $C_1$ to $C_{10}$ alkylamino, $C_1$ to $C_{10}$ substituted alkylamino, carboxamide, protected carboxamide, $C_1$ to $C_{10}$ alkylthio, $C_1$ to $C_{10}$ substituted alkylthio, $C_1$ to $C_{10}$ alkylsulfonyl, $C_1$ to $C_{10}$ substituted alkylsulfonyl, $C_1$ to $C_{10}$ alkylsulfoxide, $C_1$ to $C_{10}$ substituted alkylsulfoxide, phenylthio, substituted phenylthio, phenylsulfoxide, substituted phenylsulfoxide, phenylsulfonyl or substituted phenylsulfonyl;

$R_5$ is the formula —DWE—, wherein
  (i) D and E are each —NH— and W is $C_2$ to $C_{12}$ alkylene, $C_2$ to $C_{12}$ alkenylene, $C_2$ to $C_{12}$ alkynylene, $C_2$ to $C_{12}$ substituted alkylene, $C_2$ to $C_{12}$ substituted alkenylene, $C_2$ to $C_{12}$ substituted alkynylene, $C_7$ to $C_{18}$ phenylalkylene, $C_7$ to $C_{18}$ substituted phenylalkylene, $C_1$ to $C_{12}$ heterocycloalkylene and $C_1$ to $C_{12}$ substituted heterocycloalkylene phenylene, substituted phenylene, $C_3$ to $C_7$ cycloalkylene, $C_3$ to $C_7$ substituted cycloalkylene, $C_5$ to $C_7$ cycloalkenylene, $C_5$ to $C_7$ substituted cycloalkenylene, heterocyclene or substituted heterocyclene; or
  (ii) D is —NH— and W and E together form a non-aromatic heterocyclene or substituted non-aromatic heterocyclene having at least one ring nitrogen atom that is directly attached to X—$R_6$ depicted in the above formula; or
  (iii) E is —NH— and D and W together form a non-aromatic heterocyclene or substituted non-aromatic heterocyclene having at least one ring nitrogen atom that is directly attached to the pyridine depicted in the above formula; or
  (iv) D, W and E together form a non-aromatic heterocyclene or substituted non-aromatic heterocyclene having at least two ring nitrogen atoms, one ring nitrogen atom directly attached to X—$R_6$ depicted in the above formula and the other ring nitrogen atom directly attached to the pyridine depicted in the above formula; or
  (v) D, W and E together form a bicyclic non-aromatic heterocyclene or bicyclic substituted non-aromatic heterocyclene, each heterocyclene having at least one ring nitrogen atom, the nitrogen atom of one ring directly attached to X—$R_6$ depicted in the above formula and the nitrogen atom of the other ring directly attached to the pyridine depicted in the above formula; and $R_6$ is a hydrogen atom, $C_1$ to $C_{12}$ alkyl, $C_1$ to $C_{12}$ substituted alkyl, $C_2$ to $C_{12}$ alkenyl, $C_2$ to $C_{12}$ substituted alkenyl, phenyl, substituted phenyl, naphthyl, substituted naphthyl, $C_7$ to $C_{18}$ phenylalkyl, $C_7$ to $C_{18}$ substituted phenylalkyl, $C_1$ to $C_{12}$ heterocycloalkyl, $C_1$ to $C_{12}$ substituted heterocycloalkyl, heteroaryl, substituted heteroaryl, heterocycle or substituted heterocycle;

wherein $R_7$ or $R_8$ can be attached to a functionalized resin; or a pharmaceutically acceptable salt of a compound thereof.

In one embodiment, $R_7$ is not a hydrogen atom.

In another embodiment, $R_8$ is a hydrogen atom.

In a further embodiment, one, more or all X's are each a carbonyl group (—C(O)—).

In an additional embodiment, $R_2$ is the formula —X—NH—$R_7$, wherein X is —C(O)— and $R_7$ is $C_1$ to $C_{12}$ alkyl, $C_1$ to $C_{12}$ substituted alkyl, $C_3$ to $C_7$ cycloalkyl, $C_3$ to $C_7$ substituted cycloalkyl, $C_7$ to $C_{18}$ phenylalkyl, $C_7$ to $C_{18}$ substituted phenylalkyl, $C_1$ to $C_{12}$ heterocycloalkyl or $C_1$ to $C_{12}$ substituted heterocycloalkyl.

In another embodiment, $R_1$, $R_3$ and $R_4$ are each a hydrogen atom.

An additional embodiment provides that $R_5$ is the formula —DWE—, wherein
  (i) D and E are each —NH— and W is $C_2$ to $C_{12}$ alkylene or $C_2$ to $C_{12}$ substituted alkylene; or
  (ii) D, W and E together form a non-aromatic heterocyclene or substituted non-aromatic heterocyclene having at least two ring nitrogen atoms, one ring nitrogen atom directly attached to X—$R_6$ depicted in the above formula and the other ring nitrogen atom directly attached to the pyridine depicted in the above formula.

In a further embodiment, $R_6$ is $C_1$ to $C_{12}$ alkyl, $C_1$ to $C_{12}$ substituted alkyl, $C_2$ to $C_{12}$ alkenyl, $C_2$ to $C_{12}$ substituted alkenyl, phenyl, substituted phenyl, $C_7$ to $C_{18}$ phenylalkyl, $C_7$ to $C_{18}$ substituted phenylalkyl, $C_1$ to $C_{12}$ heterocycloalkyl, $C_1$ to $C_{12}$ substituted heterocycloalkyl, heteroaryl, substituted heteroaryl, heterocycle or substituted heterocycle.

In another embodiment,

X is —C(O)—;

$R_2$ is the formula —X—NH—$R_7$, wherein X is —C(O)— and $R_7$ is 3-(2-oxo-1-pyrrolidino)propyl, 2,4-dichlorophenethyl, 3-(1-imidazolyl)propyl, isopropyl, 1-benzyl-4-piperidinyl, 2-(2-chlorophenyl)ethyl, cyclopropyl, 2-(N-(3-methylphenyl)ethylamino)ethyl, 2-(3-chlorophenyl)ethyl, 2-(4-imidazolyl)ethyl, 2-(4-chlorophenyl)ethyl, 1-methyl-3-phenylpropyl, 2-(5- diethylamino)pentyl, 3,4-dimethoxyphenethyl, 2-(3-indolyl)ethyl, amyl, 3-butoxypropyl, cyclopentyl, heptyl, 1-ethoxycarbonyl-4-piperidinyl, sec-butyl, 1-methoxy-2-propyl, 3-methyl-2-butyl, 2-heptyl, 4-methyl-2-pentyl, 5-methyl-2-hexyl, 1-methoxy-2-butyl, 2-octyl, cyclobutyl, 3-pentyl, 3-(di-N-butylamino)propyl, butyl, n-octyl, isoamyl, 3-(N,N-dimethylamino)propyl, 3-(N-methylanilino)aminopropyl, tetrahydrofurfuryl, 3-ethoxypropyl, 4-phenylbutyl, 2-(1-pyrrolidino)ethyl, 3-(4-morpholino)propyl, 3-(2-methylpiperidino)propyl, 2-(1-methylpyrrolidin-2-yl)ethyl, 3-(diethylamino)propyl, 3-(methylthio)propyl, 3-(1-pyrrolidino)propyl, cyclohexyl, 2-(1-piperidino)ethyl, 2-(4-morpholino)ethyl, phenethyl, 3-phenylpropyl, cycloheptyl, 3-(4-methylpiperazin-1-yl)propyl, 4-methylcyclohexyl, 2-(2-pyridinyl)ethyl, neopentyl, 2-(4-methoxyphenyl)ethyl, 2-methylcyclohexyl, 3-methylcyclohexyl, allyl, (1-ethylpyrrolidin-2-yl))methyl or (3-pyridinyl)methyl;

$R_1$, $R_3$ and $R_4$ are each a hydrogen atom;

$R_5$ is butylene or 1,4-piperidylene; and $R_6$ is 3-methoxy-2-nitrophenyl, 3,5-bis(trifluoromethyl)phenyl, 5-methoxy-2-nitrophenyl, 2-methoxy-4-nitrophenyl, 4-(trifluoromethoxy)phenyl, 2,3,4,5-tetrafluorophenyl, (N-methylbenzamido)methyl, pentamethylphenyl, 3-indazolyl, 2,6-dichloro-3-pyridinyl, 2,4-dichlorophenyl, 2,5-dichlorophenyl, 3,5-dichlorophenyl, 2-chromonyl, 2-(trifluoromethyl)styryl, 4-iodophenyl, (1-methylindo-3-yl)methyl, 2-chloro-6-fluorobenzyl, (1-naphthyl)methyl, 3,4-difluorophenethyl, 4-fluoro-3-nitrophenyl, 2-bromo-5-methoxyphenyl, 4-chloro-a-methylphenethyl, 2,6-dimethoxyphenyl, 2-methyl-3-nitrophenyl, 3-methyl-4-nitrophenyl, 2-nitrophenethyl, 2-methyl-6-nitrophenyl, 5-methyl-2-nitrophenyl, 3-oxo-1-indanyl, 2-pyrazinyl, 1-methylindol-3-yl, 1-isoquinolinyl, 1-acetylpiperidin-4-yl, pyrimidin-2-ylthiomethyl, 2,2-dichloro-1-methylcyclopropyl, o-nitrophenyl, 3-cyanophenyl, 4-methyl-1,2,3-thiadiazol-5-yl, 2,4,6-trimethylphenyl, 2-(phenyl)propyl, 3-methyl-2-thienyl, 2,5-dimethylbenzyl, trans-2-phenyl-1-cyclopropyl, 2-chloro-3-pyridinyl, phenoxymethyl, 2,4-dimethylphenyl, o-methylbenzyl, p-methylbenzyl, 2-bromophenyl, cyclohexylmethyl, 3-methylthien-2-yl, 5-methylthien-2-yl, (3-thienyl)methyl, 2-methylpyrazin-5-yl, 2-methyl-2-pentyl, cyclohexyl, 3-cyclohexylpropyl, 3-thienyl, 5-methylisoxazol-4-yl, 5-methylisoxazol-3-yl, 2-methyl-3-furyl, 2-pyridinyl, 3-pentyl, 1-(2,2-dimethyl)propyl, 1-(2-methyl)butyl, 2-acetylethyl, 2-tetrahydrofuryl, trifluoromethyl, 2-furyl, 3-furyl, ethoxymethyl, 3-phthalidylmethyl, sec-butyl, tert-butyl, 1-butyl, cyclopentylmethyl, cyclobutyl, methoxymethyl or ethyl.

The invention also provides methods of preparing pyridine carboxamide or sulfonamide derivative compounds and combinatorial libraries. In one method, such compounds can be prepared by:

(a) reacting an amine containing the group variable—NH— with a pyridine that is substituted with a halo at the 6 position and is also substituted with a carboxy or sulfonyl group at one of the other positions of the pyridine ring, resulting in a pyridine that is substituted with a halo at the 6 position and is also substituted with a substituted carboxamide or sulfonamide containing, respectively, the group —C(O)—N(variable)- or the group —S(O$_2$)—N(variable)- at one of the other positions, wherein, respectively, the carboxamide carbon or the sulfur atom is directly attached to the pyridine ring; and (b) displacing the halo of the pyridine resulting from step (a) with (i) a diamine of the formula amino-variable-amino; (ii) an amino attached to a non-aromatic heterocycle or substituted heterocycle having at least one ring nitrogen atom; (iii) a non-aromatic heterocycle or substituted heterocycle having at least two ring nitrogen atoms; or (iv) a bicyclic non-aromatic heterocycle or substituted heterocycle, wherein each non-aromatic heterocycle or substituted heterocycle has at least one ring nitrogen atom. The resulting substituent is then of the formula (i) —NH-variable-amino; (ii) —NH-heterocycle; —NH-substituted heterocycle; heterocyclene-amino; or substituted heterocyclene-amino; (iii) heterocyclene; substituted heterocyclene; or (iv) a bicyclic moiety where one or both rings is heterocyclene or substituted heterocyclene.

Moreover, the terminal amino or imino group of the substituted pyridine resulting from step (b) described above can be reacted with a carboxylic acid of the formula variable—COOH, resulting in the substitution containing the group of the formula —NH-variable—NH—C(O)-variable or the formula ring nitrogen-variable—NH—C(O)-variable at that position of the pyridine ring.

In addition, the amine described above can be attached to solid support before undergoing step (a) described above.

In a further embodiment of the above-described methods, before undergoing step (a), the above-described pyridine compound can be substituted with a carboxamide group at the 3 position of the pyridine ring.

When the above-described compounds include one or more chiral centers, the stereochemistry of such chiral centers can independently be in the R or S configuration, or a mixture of the two. The chiral centers can be further designated as R or S or R,S or d,D, l,L or d,l, D,L.

Regarding the compounds and combinatorial libraries described herein, the suffix "ene" added to any of the described terms means that two parts of the substituent are each connected to two other parts in the compound (unless the substituent contains only one carbon, in which case such carbon is connected to two other parts in the compound, for example, methylene).

The term "$C_1$ to $C_{12}$ alkyl" denotes such radicals as methyl, ethyl, n-propyl, isopropyl, n-butyl, iso-butyl, sec-butyl, tert-butyl, amyl, tert-amyl, hexyl, heptyl, octyl, nonyl, decyl, undecyl, dodecyl and the like. Preferred "$C_1$ to $C_{12}$ alkyl" groups are methyl, ethyl, iso-butyl, sec-butyl and iso-propyl. Similarly, the term "$C_1$ to $C_{12}$ alkylene" denotes radicals of 1 to 12 carbons connected to two other parts in the compound.

The term "$C_2$ to $C_{12}$ alkenyl" denotes such radicals as vinyl, allyl, 2-butenyl, 3-butenyl, 2-pentenyl, 3-pentenyl, 4-pentenyl, 2-hexenyl, 3-hexenyl, 4-hexenyl, 5-hexenyl, 2-heptenyl, 3-heptenyl, 4-heptenyl, 5-heptenyl, 6-heptenyl, (as well as octenyl, nonenyl, decenyl, undecenyl, dodecenyl radicals attached at any appropriate carbon position and the like) as well as dienes and trienes of straight and branched chains.

The term "$C_2$ to $C_{12}$ alkynyl" denotes such radicals as ethanol, propynyl, 2-butynyl, 2-pentynyl, 3-pentynyl, 2-hexynyl, 3-hexynyl, 4-hexyhyl, 2-heptynyl, 3-heptynyl, 4-heptynyl, 5-heptynyl (as well as octynyl, nonynyl, decynyl, undecynyl, dodecynyl radicals attached at any appropriate carbon position and the like) as well as di- and tri-ynes of straight and branched chains.

The terms "$C_1$ to $C_{12}$ substituted alkyl," "$C_2$ to $C_{12}$ substituted alkenyl," "$C_2$ to $C_{12}$ substituted alkynyl," "$C_1$ to $C_{12}$ substituted alkylene," "$C_2$ to $C_{12}$ substituted alkenylene" and "$C_2$ to $C_{12}$ substituted alkynylene" denote groups are substituted by one or more, and preferably one or two, halogen, hydroxy, protected hydroxy, oxo, protected oxo, $C_3$ to $C_7$ cycloalkyl, phenyl, naphthyl, amino, protected amino, (monosubstituted)amino, protected (monosubstituted)amino, (disubstituted)amino, guanidino, protected guanidino, heterocyclic ring, substituted heterocyclic ring, imidazolyl, indolyl, pyrrolidinyl, $C_1$ to $C_{12}$ alkoxy, $C_1$ to $C_{12}$ acyl, $C_1$ to $C_{12}$ acyloxy, nitro, carboxy, protected carboxy, carbamoyl, carboxamide, protected carboxamide, N—($C_1$ to $C_{12}$ alkyl)carboxamide, protected N—($C_1$ to $C_{12}$ alkyl)carboxamide, N,N-di($C_1$ to $C_{12}$ alkyl)carboxamide, cyano, methylsulfonylamino, thiol, $C_1$ to $C_{10}$ alkylthio or $C_1$ to $C_{10}$ alkylsulfonyl groups. The substituted alkyl groups may be substituted once or more, and preferably once or twice, with the same or with different substituents.

Examples of the above substituted alkyl groups include the 2-oxo-prop-1-yl, 3-oxo-but-1-yl, cyanomethyl, nitromethyl, chloromethyl, hydroxymethyl, tetrahydropyranyloxymethyl, trityloxymethyl, propionyloxymethyl, aminomethyl, carboxymethyl, allyloxycarbonylmethyl, allyloxycarbonylaminomethyl, methoxymethyl, ethoxymethyl, t-butoxymethyl, acetoxymethyl, chloromethyl, bromomethyl, iodomethyl, trifluoromethyl, 6-hydroxyhexyl, 2,4-dichloro(n-butyl), 2-aminopropyl, 1-chioroethyl, 2-chloroethyl, 1-bromoethyl, 2-chloroethyl, 1-fluoroethyl, 2-fluoroethyl, 1-iodoethyl, 2-iodoethyl, 1-chloropropyl, 2-chloropropyl, 3-chloropropyl, 1-bromopropyl, 2-bromopropyl, 3-bromopropyl, 1-fluoropropyl, 2-fluoropropyl, 3-fluoropropyl, 1-iodopropyl, 2-iodopropyl, 3-iodopropyl, 2-aminoethyl, 1-aminoethyl, N-benzoyl-2-aminoethyl, N-acetyl-2-aminoethyl, N-benzoyl-1-aminoethyl, N-acetyl-1-aminoethyl and the like.

Examples of the above substituted alkenyl groups include styrenyl, 3-chloro-propen-1-yl, 3-chloro-buten-1-yl, 3-methoxy-propen-2-yl, 3-phenyl-buten-2-yl, 1-cyano-buten-3-yl and the like. The geometrical isomerism is not critical, and all geometrical isomers for a given substituted alkenyl can be used.

Examples of the above substituted alkynyl groups include phenylacetylen-1-yl, 1-phenyl-2-propyn-1-yl and the like.

The term "oxo" denotes a carbon atom bonded to two additional carbon atoms substituted with an oxygen atom doubly bonded to the carbon atom, thereby forming a ketone moiety.

The term "protected oxo" denotes a carbon atom bonded to two additional carbon atoms substituted with two alkoxy groups or twice bonded to a substituted diol moiety, thereby forming an acyclic or cyclic ketal moiety.

The term "$C_1$ to $C_{12}$ alkoxy" as used herein denotes groups such as methoxy, ethoxy, n-propoxy, isopropoxy, n-butoxy, t-butoxy and like groups. A preferred alkoxy is methoxy. The term "$C_1$ to $C_{12}$ substituted alkoxy" means the alkyl portion of the alkoxy can be substituted in the same manner as in relation to $C_1$ to $C_{12}$ substituted alkyl. Similarly, the term "$C_1$ to $C_{12}$ phenylalkoxy" as used herein means "$C_1$ to $C_{12}$ alkoxy" bonded to a phenyl radical.

The term "$C_1$ to $C_{12}$ acyloxy" denotes herein groups such as formyloxy, acetoxy, propionyloxy, butyryloxy, pivaloyloxy, pentanoyloxy, hexanoyloxy, heptanoyloxy, octanoyloxy, nonanoyloxy, decanoyloxy, undecanoyloxy, dodecanoyloxy and the like.

Similarly, the term "$C_1$ to $C_{12}$ acyl" encompasses groups such as formyl, acetyl, propionyl, butyryl, pentanoyl, pivaloyl, hexanoyl, heptanoyl, octanoyl, nonanoyl, decanoyl, undecanoyl, dodecanoyl, benzoyl and the like. Preferred acyl groups are acetyl and benzoyl.

The term "$C_1$ to $C_{12}$ substituted acyl" denotes the acyl group substituted by one or more, and preferably one or two, halogen, hydroxy, protected hydroxy, oxo, protected oxo, cyclohexyl, naphthyl, amino, protected amino, (monosubstituted)amino, protected (monosubstituted)amino, (disubstituted)amino, guanidino, heterocyclic ring, substituted heterocyclic ring, imidazolyl, indolyl, pyrrolidinyl, $C_1$ to $C_{12}$ alkoxy, $C_1$ to $C_{12}$ acyl, $C_1$ to $C_{12}$ acyloxy, nitro, $C_1$ to $C_{12}$ alkyl ester, carboxy, protected carboxy, carbamoyl, carboxamide, protected carboxamide, N—($C_1$ to $C_{12}$ alkyl)carboxamide, protected N—($C_1$ to $C_{12}$ alkyl)carboxamide, N,N-di($C_1$ to $C_{12}$ alkyl)carboxamide, cyano, methylsulfonylamino, thiol, $C_1$ to $C_{10}$ alkylthio or $C_1$ to $C_{10}$ alkylsulfonyl groups. The substituted acyl groups may be substituted once or more, and preferably once or twice, with the same or with different substituents.

Examples of $C_1$ to $C_{12}$ substituted acyl groups include 4-phenylbutyroyl, 3-phenylbutyroyl, 3-phenylpropanoyl, 2-cyclohexanylacetyl, cyclohexanecarbonyl, 2-furanoyl and 3-dimethylaminobenzoyl.

The substituent term "$C_3$ to $C_7$ cycloalkyl" includes the cyclopropyl, cyclobutyl, cyclopentyl, cyclohexyl or cycloheptyl rings. Similarly, a substituent that can be $C_3$ to $C_7$ cycloalkyl" can also be "$C_5$ to $C_7$ cycloalkyl," which includes the cyclopentyl, cyclohexyl or cycloheptyl rings.

The substituent term "$C_3$ to $C_7$ substituted cycloalkyl" or "$C_5$ to $C_7$ substituted cycloalkyl" indicates the above cycloalkyl rings substituted by one or two halogen, hydroxy, protected hydroxy, $C_1$ to $C_{10}$ alkylthio, $C_1$ to $C_{10}$ alkylsulfoxide, $C_1$ to $C_{10}$ alkylsulfonyl, $C_1$ to $C_{10}$ substituted alkylthio, $C_1$ to $C_{10}$ substituted alkylsulfoxide, $C_1$ to $C_{10}$ substituted alkylsulfonyl, $C_1$ to $C_{12}$ alkyl, $C_1$ to $C_{12}$ alkoxy, $C_1$ to $C_{12}$ substituted alkyl, $C_1$ to $C_{12}$ alkoxy, oxo, protected oxo, (monosubstituted)amino, (disubstituted)amino, trifluoromethyl, carboxy, protected carboxy, phenyl, substituted phenyl, phenylthio, phenylsulfoxide, phenylsulfonyl, amino, or protected amino groups.

The term "cycloalkylene" means a cycloalkyl, as defined above, where the cycloalkyl radical is bonded at two positions connecting together two separate additional groups. Similarly, the term "substituted cycloalkylene" means a cycloalkylene where the cycloalkyl radical is bonded at two positions connecting together two separate additional groups and further bearing at least one additional substituent.

The term "$C_5$ to $C_7$ cycloalkenyl" indicates a 1,2, or 3-cyclopentenyl ring, a 1,2,3 or 4-cyclohexenyl ring or a 1,2,3,4 or 5-cycloheptenyl ring, while the term "substituted $C_5$ to $C_7$ cycloalkenyl" denotes the above $C_5$ to $C_7$ cycloalkenyl rings substituted by a $C_1$ to $C_{12}$ alkyl radical, halogen, hydroxy, protected hydroxy, $C_1$ to $C_{12}$ alkoxy, trifluoromethyl, carboxy, protected carboxy, oxo, protected oxo, (monosubstituted)amino, protected (monosubstituted)amino, (disubstituted)amino, phenyl, substituted phenyl, amino, or protected amino.

The term "$C_5$ to $C_7$ cycloalkenylene" is a cycloalkenyl ring, as defined above, where the cycloalkenyl radical is bonded at two positions connecting together two separate additional groups. Examples of $C_5$ to $C_7$ cycloalkenylenes include 1,3-cyclopentylene and 1,2-cyclohexylene.

Similarly, the term "substituted $C_5$ to $C_7$ cycloalkenylene" means a cycloalkenylene further substituted by halogen, hydroxy, protected hydroxy, $C_1$ to $C_{10}$ alkylthio, $C_1$ to $C_{10}$ alkylsulfoxide, $C_1$ to $C_{10}$ alkylsulfonyl, $C_1$ to $C_{10}$ substituted alkylthio, $C_1$ to $C_{10}$ substituted alkylsulfoxide, $C_1$ to $C_{10}$ substituted alkylsulfonyl, $C_1$ to $C_{12}$ alkyl, $C_1$ to $C_{12}$ alkoxy, $C_1$ to $C_{12}$ substituted alkyl, $C_1$ to $C_{12}$ alkoxy, oxo, protected oxo, (monosubstituted)amino, (disubstituted)amino, trifluoromethyl, carboxy, protected carboxy, phenyl, substituted phenyl, phenylthio, phenylsulfoxide, phenylsulfonyl, amino, or protected amino group. Examples of substituted $C_5$ to $C_7$ cycloalkenylenes include 4-chloro-1,3-cyclopentylene and 4-methyl-1,2-cyclohexylene.

The term "heterocycle" or "heterocyclic ring" denotes optionally substituted five-membered to eight-membered rings that have 1 to 4 heteroatoms, such as oxygen, sulfur and/or nitrogen, in particular nitrogen, either alone or in conjunction with sulfur or oxygen ring atoms. These five-membered to eight-membered rings may be saturated, fully unsaturated or partially unsaturated, with fully saturated rings being preferred. Preferred heterocyclic rings include morpholino, piperidinyl, piperazinyl, 2-amino-imidazoyl, tetrahydrofurano, pyrrolo, tetrahydrothiophen-yl, hexylmethyleneimino and heptylmethyleneimino.

The term "substituted heterocycle" or "substituted heterocyclic ring" means the above-described heterocyclic ring is substituted with, for example, one or more, and preferably one or two, substituents which are the same or different which substituents can be halogen, hydroxy, protected hydroxy, cyano, nitro, $C_1$ to $C_{12}$ alkyl, $C_1$ to $C_{12}$ alkoxy, $C_1$ to $C_{12}$ substituted alkoxy, $C_1$ to $C_{12}$ acyl, $C_1$ to $C_{12}$ acyloxy, carboxy, protected carboxy, carboxymethyl, protected carboxymethyl, hydroxymethyl, protected hydroxymethyl, amino, protected amino, (monosubstituted) amino, protected (monosubstituted) amino, (disubstituted)amino carboxamide, protected carboxamide, N—($C_1$ to $C_{12}$ alkyl) carboxamide, protected N—($C_1$ to $C_{12}$ alkyl)carboxamide, N, N-di($C_1$ to $C_{12}$ alkyl)carboxamide, trifluoromethyl, N—(($C_1$ to $C_{12}$ alkyl)sulfonyl)amino, N-(phenylsulfonyl) amino, heterocycle or substituted heterocycle groups.

The term "heteroaryl" means a heterocyclic aromatic derivative which is a five-membered or six-membered ring system having from 1 to 4 heteroatoms, such as oxygen, sulfur and/or nitrogen, in particular nitrogen, either alone or in conjunction with sulfur or oxygen ring atoms. Examples of heteroaryls include pyridinyl, pyrimidinyl, and pyrazinyl, pyridazinyl, pyrrolo, furano, oxazolo, isoxazolo, phthalimido, thiazolo and the like.

The term "substituted heteroaryl" means the above-described heteroaryl is substituted with, for example, one or more, and preferably one or two, substituents which are the same or different which substituents can be halogen, hydroxy, protected hydroxy, cyano, nitro, $C_1$ to $C_{12}$ alkyl, $C_1$ to $C_{12}$ alkoxy, $C_1$ to $C_{12}$ substituted alkoxy, $C_1$ to $C_{12}$ acyl, $C_1$ to $C_{12}$ substituted acyl, $C_1$ to $C_{12}$ acyloxy, carboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N—($C_1$ to $C_{12}$ alkyl) carboxamide, protected N—($C_1$ to $C_{12}$ alkyl)carboxamide, N, N-di($C_1$ to $C_{12}$ alkyl)carboxamide, trifluoromethyl, N—(($C_1$ to $C_{12}$ alkyl)sulfonyl)amino or N-(phenylsulfonyl) amino groups.

The term "$C_7$ to $C_{18}$ phenylalkyl" denotes a $C_1$ to $C_{12}$ alkyl group substituted at any position within the alkyl chain by a phenyl. The definition includes groups of the formula: -phenyl-alkyl, -alkyl-phenyl and -alkyl-phenyl-alkyl. Examples of such a group include benzyl, 2-phenylethyl, 3-phenyl(n-propyl), 4-phenylhexyl, 3-phenyl(n-amyl), 3-phenyl(sec-butyl) and the like. Preferred $C_7$ to $C_{18}$ phenylalkyl groups are any one of the preferred alkyl groups described herein combined with a phenyl group.

Similarly, the term "$C_1$ to $C_{12}$ heterocycloalkyl" denotes a $C_1$ to $C_{12}$ alkyl group substituted at any position within the alkyl chain by a "heterocycle," as defined herein. The definition includes groups of the formula: -heterocyclic-alkyl, -alkyl-heterocyclic and -alkyl-heterocyclic-alkyl. Examples of such a group include 2-pyridylethyl, 3-pierydyl (n-propyl), 4-furylhexyl, 3-piperazyl(n-amyl), 3-morpholyl (sec-butyl) and the like. Preferred $C_1$ to $C_{12}$ heterocycloalkyl groups are any one of the preferred alkyl groups described herein combined with any one of the preferred heterocycle groups described herein.

The terms "$C_7$ to $C_{18}$ substituted phenylalkyl" and "$C_1$ to $C_{12}$ substituted heterocycloalkyl" denote a $C_7$ to $C_{18}$ phenylalkyl group or $C_1$ to $C_{12}$ heterocycloalkyl substituted (on the alkyl or, where applicable, phenyl or heterocyclic portion) with one or more, and preferably one or two, groups chosen from halogen, hydroxy, protected hydroxy, oxo, protected oxo, amino, protected amino, (monosubstituted) amino, protected (monosubstituted)amino, (disubstituted) amino, guanidino, protected guanidino, heterocyclic ring, substituted heterocyclic ring, $C_1$ to $C_{12}$ alkyl, $C_1$ to $C_{12}$ substituted alkyl, $C_1$ to $C_{12}$ alkoxy, $C_1$ to $C_{12}$ substituted alkoxy, $C_1$ to $C_{12}$ acyl, $C_1$ to $C_{12}$ substituted acyl, $C_1$ to $C_{12}$ acyloxy, nitro, carboxy, protected carboxy, carbamoyl, carboxamide, protected carboxamide, N—($C_1$ to $C_{12}$ alkyl) carboxamide, protected N—($C_1$ to $C_{12}$ alkyl)carboxamide, N, N—($C_1$ to $C_{12}$dialkyl)carboxamide, cyano, N—($C_1$ to $C_{12}$ alkylsulfonyl)amino, thiol, $C_1$ to $C_{10}$ alkylthio, $C_1$ to $C_{10}$ alkylsulfonyl groups; and/or the phenyl group may be substituted with one or more, and preferably one or two, substituents chosen from halogen, hydroxy, protected hydroxy, cyano, nitro, $C_1$ to $C_{12}$ alkyl, $C_1$ to $C_{12}$ substituted alkyl, $C_1$ to $C_{12}$ alkoxy, $C_1$ to $C_{12}$ substituted alkoxy, $C_1$ to $C_{12}$ acyl, $C_1$ to $C_{12}$ substituted acyl, $C_1$ to $C_{12}$ acyloxy, carboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N—($C_1$ to $C_{12}$ alkyl) carboxamide, protected N—($C_1$ to $C_{12}$ alkyl)carboxamide, N, N-di($C_1$ to $C_{12}$ alkyl)carboxamide, trifluoromethyl, N—(($C_1$ to $C_{12}$ alkyl)sulfonyl)amino, N-(phenylsulfonyl) amino, Cyclic $C_2$ to $C_{12}$ alkylene or a phenyl group, substituted or unsubstituted, for a resulting biphenyl group. The substituted alkyl, phenyl or heterocyclic groups may be substituted with one or more, and preferably one or two, substituents which can be the same or different.

Examples of the term "$C_7$ to $C_{18}$ substituted phenylalkyl" include groups such as 2-phenyl-1-chloroethyl, 2-(4-methoxyphenyl)ethyl, 4-(2,6-dihydroxy phenyl)n-hexyl, 2-(5-cyano-3-methoxyphenyl)n-pentyl, 3-(2,6-dimethylphenyl)n-propyl, 4-chloro-3-aminobenzyl, 6-(4-methoxyphenyl)-3-carboxy(n-hexyl), 5-(4-aminomethylphenyl)-3-(aminomethyl)n-pentyl, 5-phenyl-3-oxo-n-pent-1-yl and the like.

The term "$C_7$ to $C_{18}$ phenylalkylene" specifies a $C_7$ to $C_{18}$ phenylalkyl, as defined above, where the phenylalkyl radical is bonded at two different positions connecting together two separate additional groups. The definition includes groups of the formula: -phenyl-alkyl-,-alkyl-phenyl- and -alkyl-phenyl-alkyl-. Substitutions on the phenyl ring can be 1,2, 1,3 or 1,4. $C_7$ to $C_{18}$ phenylalkylenes include, for example, 1,4-toluylene and 1,3-xylylene.

Similarly, the term "$C_1$ to $C_{12}$ heterocycloalkylene" specifies a $C_1$ to $C_{12}$ heterocycloalkyl, as defined above, where the heterocycloalkyl radical is bonded at two different positions connecting together two separate additional groups. The definition includes groups of the formula: -heterocyclic-alkyl-, -alkyl-heterocyclic and -alkyl-heterocyclic-alkyl-.

The terms "$C_7$ to $C_{18}$ substituted phenylalkylene" and "$C_1$ to $C_{12}$ substituted heterocycloalkylene" means a $C_7$ to $C_{18}$ phenylalkylene or $C_1$ to $C_{12}$ heterocycloalkylene as defined above that is further substituted by halogen, hydroxy, protected hydroxy, $C_1$ to $C_{10}$ alkylthio, $C_1$ to $C_{10}$ alkylsulfoxide, $C_1$ to $C_{10}$ alkylsulfonyl, $C_1$ to $C_{10}$ substituted alkylthio, $C_1$ to $C_{10}$ substituted alkylsulfoxide, $C_1$ to $C_{10}$ substituted alkylsulfonyl, $C_1$ to $C_{12}$ alkyl, $C_1$ to $C_{12}$ alkoxy, $C_1$ to $C_{12}$ substituted alkyl, $C_1$ to $C_{12}$ alkoxy, oxo, protected oxo, (monosubstituted)amino, (disubstituted)amino, trifluoromethyl, carboxy, protected carboxy, phenyl, substituted phenyl, phenylthio, phenylsulfoxide, phenylsulfonyl, amino, or protected amino group on the phenyl ring or on the alkyl group.

The term "substituted phenyl" specifies a phenyl group substituted with one or more, and preferably one or two, moieties chosen from the groups consisting of halogen, hydroxy, protected hydroxy, cyano, nitro, $C_1$ to $C_{12}$ alkyl, $C_1$ to $C_{12}$ substituted alkyl, $C_1$ to $C_{12}$ alkoxy, $C_1$ to $C_{12}$ substituted alkoxy, $C_1$ to $C_{12}$ acyl, $C_1$ to $C_{12}$ substituted acyl, $C_1$ to $C_{12}$ acyloxy, carboxy, protected carboxy, carboxymethyl, protected carboxymethyl, hydroxymethyl, protected hydroxymethyl, amino, protected amino, (monosubstituted)amino, protected (monosubstituted) amino, (disubstituted)amino, carboxamide, protected carboxamide, N—($C_1$ to $C_{12}$ alkyl)carboxamide, protected N—($C_1$ to $C_{12}$ alkyl)carboxamide, N, N-di($C_1$ to $C_{12}$ alkyl) carboxamide, trifluoromethyl, N—(($C_1$ to $C_{12}$ alkyl) sulfonyl)amino, N-(phenylsulfonyl)amino or phenyl, wherein the phenyl is substituted or unsubstituted, such that, for example, a biphenyl results.

Examples of the term "substituted phenyl" includes a mono- or di(halo)phenyl group such as 2, 3 or 4-chlorophenyl, 2,6-dichlorophenyl, 2,5-dichlorophenyl, 3,4-dichlorophenyl, 2, 3 or 4-bromophenyl, 3,4-dibromophenyl, 3-chloro-4-fluorophenyl, 2, 3 or 4-fluorophenyl and the like; a mono or di(hydroxy)phenyl group such as 2, 3 or 4-hydroxyphenyl, 2,4-dihydroxyphenyl, the protected-hydroxy derivatives thereof and the like; a nitrophenyl group such as 2, 3 or 4-nitrophenyl; a cyanophenyl group, for example, 2, 3 or 4-cyanophenyl; a mono- or di(alkyl)phenyl group such as 2, 3 or 4-methylphenyl, 2,4-dimethylphenyl, 2, 3 or 4-(isopropyl)phenyl, 2, 3 or 4-ethylphenyl, 2, 3 or 4-(n-propyl) phenyl and the like; a mono or di(alkoxyl)phenyl group, for example, 2,6-dimethoxyphenyl, 2, 3 or 4-methoxyphenyl, 2, 3 or 4-ethoxyphenyl, 2, 3 or 4-(isopropoxy)phenyl, 2, 3 or 4-(t-butoxy)phenyl, 3-ethoxy-4-methoxyphenyl and the like; 2, 3 or 4-trifluoromethylphenyl; a mono- or dicarboxyphenyl or (protected carboxy)phenyl group such as 2, 3 or 4-carboxyphenyl or 2,4-di(protected carboxy)phenyl; a mono- or di(hydroxymethyl)phenyl or (protected hydroxymethyl)phenyl such as 2, 3, or 4-(protected hydroxymethyl)phenyl or 3,4-di(hydroxymethyl)phenyl; a mono- or di(aminomethyl)phenyl or (protected aminomethyl)phenyl such as 2, 3 or 4-(aminomethyl)phenyl or 2,4-(protected aminomethyl)phenyl; or a mono- or di(N-(methylsulfonylamino))phenyl such as 2, 3 or 4-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy 4-chlorophenyl and the like.

The term "phenoxy" denotes a phenyl bonded to an oxygen atom, wherein the binding to the rest of the molecule is through the oxygen atom. The term "substituted phenoxy" specifies a phenoxy group substituted with one or more, and preferably one or two, moieties chosen from the groups consisting of halogen, hydroxy, protected hydroxy, cyano, nitro, $C_1$ to $C_{12}$ alkyl, $C_1$ to $C_{12}$ alkoxy, $C_1$ to $C_{12}$ substituted alkoxy, $C_1$ to $C_{12}$ acyl, $C_1$ to $C_{12}$ acyloxy, carboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N—($C_1$ to $C_{12}$ alkyl) carboxamide, protected N—($C_1$ to $C_{12}$ alkyl)carboxamide, N, N-di($C_1$ to $C_{12}$ alkyl)carboxamide, trifluoromethyl, N—(($C_1$ to $C_{12}$ alkyl)sulfonyl)amino and N-(phenylsulfonyl)amino.

Examples of substituted phenoxy include 2-methylphenoxy, 2-ethylphenoxy, 2-propylphenoxy, 2-isopropylphenoxy, 2-sec-butylphenoxy, 2-tert-butylphenoxy, 2-allylphenoxy, 2-propenylphenoxy, 2-cyclopentylphenoxy, 2-fluorophenoxy, 2-(trifluoromethyl) phenoxy, 2-chlorophenoxy, 2-bromophenoxy, 2-methoxyphenoxy, 2-ethoxyphenoxy, 2-isopropoxyphenoxy, 3-methylphenoxy, 3-ethylphenoxy, 3-isopropylphenoxy, 3-tert-butylphenoxy, 3-pentadecylphenoxy, 3-(trifluoromethyl)phenoxy, 3-fluorophenoxy, 3-chlorophenoxy, 3-bromophenoxy, 3-iodophenoxy, 3-methoxyphenoxy, 3-(trifluoromethoxy) phenoxy, 4-methylphenoxy, 4-ethylphenoxy, 4-propylphenoxy, 4-isopropylphenoxy, 4-sec-butylphenoxy, 4-tert-butylphenoxy, 4-tert-amylphenoxy, 4-nonylphenoxy, 4-dodecylphenoxy, 4-cyclopenylphenoxy, 4-(trifluoromethyl)phenoxy, 4-fluorophenoxy, 4-chlorophenoxy, 4-bromophenoxy, 4-iodophenoxy, 4-methoxyphenoxy, 4-(trifluoromethoxy)phenoxy, 4-ethoxyphenoxy, 4-propoxyphenoxy, 4-butoxyphenoxy, 4-hexyloxyphenoxy, 4-heptyloxyphenoxy, 2,3-dimethylphenoxy, 5,6,7,8-tetrahydro-1-naphthoxy, 2,3-dichlorophenoxy, 2,3-dihydro-2,2-dimethyl-7-benzofuranoxy, 2,3-dimethoxyphenoxy, 2,6-dimethylphenoxy, 2,6-diisopropylphenoxy, 2,6-di-sec-butylphenoxy, 2-tert-butyl-6-methylphenoxy, 2,6-di-tert-butylphenoxy, 2-allyl-6-methylphenoxy, 2,6-difluorophenoxy, 2,3-difluorophenoxy, 2,6-dichlorophenoxy, 2,6-dibromophenoxy, 2-fluoro-6-methoxyphenoxy, 2,6-dimethoxyphenoxy, 3,5-dimethylphenoxy, 5-isopropyl-3-methylphenoxy, 3,5-di-tert-butylphenoxy, 3,5-bis(trifluoromethyl)phenoxy, 3,5-difluorophenoxy, 3,5-dichlorophenoxy, 3,5-dimethoxyphenoxy, 3-chloro-5-methoxyphenoxy, 3,4-dimethylphenoxy, 5-indanoxy, 5,6,7,8-tetrahydro-2-naphthoxy, 4-chloro-3-methylphenoxy, 2,4-dimethylphenoxy, 2,5-dimethylphenoxy, 2-isopropyl-5-methylphenoxy, 4-isopropyl-3-methylphenoxy, 5-isopropyl-2-methylphenoxy, 2-tert-butyl-5-methylphenoxy, 2-tert-butyl-4-methylphenoxy, 2,4-di-tert-butylphenoxy, 2,4-di-tert-amylphenoxy, 4-fluoro-2-methylphenoxy, 4-fluoro-3-methylphenoxy, 2-chloro-4-methylphenoxy, 2-chloro-5-methylphenoxy, 4-chloro-2-methylphenoxy, 4-chloro-3-ethylphenoxy, 2-bromo-4-methylphenoxy, 4-iodo-2-methylphenoxy, 2-chloro-5-(trifluoromethyl)phenoxy, 2,4-difluorophenoxy, 2,5-difluorophenoxy, 3,4-difluorophenoxy, 4-chloro-2-fluorophenoxy, 3-chloro-4-fluorophenoxy, 4-chloro-3-fluorophenoxy, 2-bromo-4-fluorophenoxy, 4-bromo-2-fluorophenoxy, 2-bromo-5-fluorophenoxy, 2,4- dichlorophenoxy, 3,4-dichlorophenoxy, 2,5-dichlorophenoxy, 2-bromo-4-chlorophenoxy, 2-chloro-4-fluorophenoxy, 4-bromo-2-chlorophenoxy, 2,4-dibromophenoxy, 2-methoxy-4-methylphenoxy, 4-allyl-2-methylphenoxy, trans-2-ethoxy-5-(1-propenyl)phenoxy, 2-methoxy-4-propenylphenoxy, 3,4-dimethoxyphenoxy, 3-ethoxy-4-methoxyphenoxy, 4-allyl-2,6-dimethoxyphenoxy, 3,4-methylenedioxyphenoxy, 2,3,6-trimethylphenoxy, 2,4-dichloro-3-methylphenoxy, 2,3,4-trifluorophenoxy, 2,3,6-trifluorophenoxy, 2,3,5-trifluorophenoxy, 2,3,4-trichlorophenoxy, 2,3,6-trichlorophenoxy, 2,3,5-trimethylphenoxy, 3,4,5-trimethylphenoxy, 4-chloro-3,5-dimethylphenoxy, 4-bromo-3,5-dimethylphenoxy, 2,4,6-trimethylphenoxy, 2,6-bis(hydroxymethyl)-4-methylphenoxy, 2,16,-di-tert-butyl-4-methylphenoxy, 2,6-di-tert-butyl-4-methoxyphenoxy, 2,4,5-trifluorophenoxy, 2-chloro-3,5-difluorophenoxy, 2,4,6-trichlorophenoxy, 3,4,5-trimethoxyphenoxy, 2,3,5-trichlorophenoxy, 4-bromo-2,6-dimethylphenoxy, 4-bromo-6-chloro-2-methylphenoxy, 2,6-dibromo-4-methylphenoxy, 2,6-dichloro-4-fluorophenoxy, 2,6-dibromo-4-fluorophenoxy, 2,4,6-tribromophenoxy, 2,4,6-triiodophenoxy, 2-chloro-4,5-dimethylphenoxy, 4-chloro-2-isopropyl-5-methylphenoxy, 2-bromo-4,5-difluorophenoxy, 2,4,5-trichlorophenoxy, 2,3,5,6-tetrafluorophenoxy and the like.

The term "$C_7$ to $C_{18}$ substituted phenylalkoxy" denotes a $C_7$ to $C_{18}$ phenylalkoxy group bonded to the rest of the molecule through the oxygen atom, wherein the phenylalkyl portion is substituted with one or more, and preferably one or two, groups selected from halogen, hydroxy, protected hydroxy, oxo, protected oxo, amino, protected amino, (monosubstituted)amino, protected (monosubstituted) amino, (disubstituted)amino, guanidino, heterocyclic ring, substituted heterocyclic ring, $C_1$ to $C_{12}$ alkoxy, $C_1$ to $C_{12}$ acyl, $C_1$ to $C_{12}$ acyloxy, nitro, carboxy, protected carboxy, carbamoyl, carboxamide, protected carboxamide, N—($C_1$ to $C_{12}$ alkyl)carboxamide, protected N—($C_1$ to $C_{12}$ alkyl) carboxamide, N, N—($C_1$ to $C_{12}$ dialkyl)carboxamide, cyano, N—($C_1$ to $C_{12}$ alkylsulfonyl)amino, thiol, $C_1$ to $C_{10}$ alkylthio, $C_1$ to $C_{10}$ alkylsulfonyl groups; and/or the phenyl group can be substituted with one or more, and preferably one or two, substituents chosen from halogen, hydroxy, protected hydroxy, cyano, nitro, $C_1$ to $C_{12}$ alkyl, $C_1$ to $C_{12}$ alkoxy, $C_1$ to $C_{12}$ acyl, $C_1$ to $C_{12}$ acyloxy, carboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N—($C_1$ to $C_{12}$ alkyl) carboxamide, protected N—($C_1$ to $C_2$ alkyl) carboxamide, N, N-di($C_1$ to $C_{12}$ alkyl)carboxamide, trifluoromethyl, N—(($C_1$ to $C_{12}$ alkyl)sulfonyl)amino, N-(phenylsulfonyl) amino or a phenyl group, substituted or unsubstituted, for a resulting biphenyl group. The substituted alkyl or phenyl groups may be substituted with one or more, and preferably one or two, substituents which can be the same or different.

Examples of the term "$C_7$ to $C_{18}$ substituted phenylalkoxy" include groups such as 2-(4-hydroxyphenyl)ethoxy, 4-(4-methoxyphenyl)butoxy, (2R)-3-phenyl-2-amino-propoxy, (2S)-3-phenyl-2-amino-propoxy, 2-indanoxy, 6-phenyl-1-hexanoxy, cinnamyloxy, (+/−)-2-phenyl-1-propoxy, 2,2-dimethyl-3-phenyl-1-propoxy and the like.

The term "phthalimide" means a cyclic imide which is made from phthalic acid, also called 1,2-benzenedicarboxylic acid. The term "substituted phthalimide" specifies a phthalimide group substituted with one or more, and preferably one or two, moieties chosen from the groups consisting of halogen, hydroxy, protected hydroxy, cyano, nitro, $C_1$ to $C_{12}$ alkyl, $C_1$ to $C_{12}$ alkoxy, $C_1$ to $C_{12}$ substituted alkoxy, $C_1$ to $C_{12}$ acyl, $C_1$ to $C_{12}$ acyloxy, carboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N—($C_1$ to $C_{12}$ alkyl) carboxamide, protected N—($C_1$ to $C_{12}$ alkyl)carboxamide, N, N-di($C_1$ to $C_{12}$ alkyl)carboxamide, trifluoromethyl, N—(($C_1$ to $C_{12}$ alkyl)sulfonyl)amino and N-(phenylsulfonyl)amino.

Examples of substituted phthalimides include 4,5-dichlorophthalimido, 3-fluorophthalimido, 4-methoxyphthalimido, 3-methylphthalimido, 4-carboxyphthalimido and the like.

The term "substituted naphthyl" specifies a naphthyl group substituted with one or more, and preferably one or two, moieties either on the same ring or on different rings chosen from the groups consisting of halogen, hydroxy, protected hydroxy, cyano, nitro, $C_1$ to $C_6$ alkyl, $C_1$ to $C_7$ alkoxy, $C_1$ to $C_7$ acyl, $C_1$ to $C_7$ acyloxy, carboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N—($C_1$ to $C_{12}$ alkyl) carboxamide, protected N—($C_1$ to $C_{12}$ alkyl)carboxamide, N, N-di($C_1$ to $C_{12}$ alkyl)carboxamide, trifluoromethyl, N—(($C_1$ to $C_{12}$ alkyl)sulfonyl)amino or N-(phenylsulfonyl) amino.

Examples of the term "substituted naphthyl" includes a mono or di(halo)naphthyl group such as 1, 2, 3, 4, 5, 6, 7 or 8-chloronaphthyl, 2, 6-dichloronaphthyl, 2,5-dichloronaphthyl, 3,4-dichloronaphthyl, 1, 2, 3, 4, 5, 6, 7 or 8-bromonaphthyl, 3,4-dibromonaphthyl, 3-chloro-4-fluoronaphthyl, 1, 2, 3, 4, 5, 6, 7 or 8-fluoronaphthyl and the like; a mono or di(hydroxy)naphthyl group such as 1, 2, 3, 4, 5, 6, 7 or 8-hydroxynaphthyl, 2,4-dihydroxynaphthyl, the protected-hydroxy derivatives thereof and the like; a nitronaphthyl group such as 3- or 4-nitronaphthyl; a cyanonaphthyl group, for example, 1, 2, 3, 4, 5, 6, 7 or 8-cyanonaphthyl; a mono- or di(alkyl)naphthyl group such as 2, 3, 4, 5, 6, 7 or 8-methylnaphthyl, 1, 2, 4-dimethylnaphthyl, 1, 2, 3, 4, 5, 6, 7 or 8-(isopropyl)naphthyl, 1, 2, 3, 4, 5, 6, 7 or 8-ethylnaphthyl, 1, 2, 3, 4, 5, 6, 7 or 8-(n-propyl)naphthyl and the like; a mono or di(alkoxy)naphthyl group, for example, 2, 6-dimethoxynaphthyl, 1, 2, 3, 4, 5, 6, 7 or 8-methoxynaphthyl, 1, 2, 3, 4, 5, 6, 7 or 8-ethoxynaphthyl, 1, 2, 3, 4, 5, 6, 7 or 8-(isopropoxy)naphthyl, 1, 2, 3, 4, 5, 6, 7 or 8-(t-butoxy)naphthyl, 3-ethoxy-4-methoxynaphthyl and the like; 1, 2, 3, 4, 5, 6, 7 or 8-trifluoromethylnaphthyl; a mono- or dicarboxynaphthyl or (protected carboxy)naphthyl group such as 1, 2, 3, 4, 5, 6, 7 or 8-carboxynaphthyl or 2, 4-di(-protected carboxy)naphthyl; a mono-or di(hydroxymethyl)naphthyl or (protected hydroxymethyl) naphthyl such as 1, 2, 3, 4, 5, 6, 7 or 8-(protected hydroxymethyl)naphthyl or 3, 4-di(hydroxymethyl) naphthyl; a mono- or di(amino)naphthyl or (protected amino)naphthyl such as 1, 2, 3, 4, 5, 6, 7 or 8-(amino) naphthyl or 2, 4-(protected amino)-naphthyl, a mono- or di(aminomethyl)naphthyl or (protected aminomethyl) naphthyl such as 2, 3, or 4-(aminomethyl)naphthyl or 2, 4-(protected aminomethyl)-naphthyl; or a mono- or di-(N-methylsulfonylamino) naphthyl such as 1, 2, 3, 4, 5, 6, 7 or 8-(N-methylsulfonylamino)naphthyl. Also, the term "substituted naphthyl" represents disubstituted naphthyl groups wherein the substituents are different, for example, 3-methyl-4-hydroxynaphth-1-yl, 3-chloro-4-hydroxynaphth-2-yl, 2-methoxy-4-bromonaphth-1-yl, 4-ethyl-2-hydroxynaphth-1-yl, 3-hydroxy-4-nitronaphth-2-yl, 2-hydroxy-4-chloronaphth-1-yl, 2-methoxy-7-bromonaphth-1-yl, 4-ethyl-5-hydroxynaphth-2-yl, 3-hydroxy-8-nitronaphth-2-yl, 2-hydroxy-5-chloronaphth-1-yl and the like.

The term "naphthylene" means a naphthyl radical bonded at two positions connecting together two separate additional groups. Similarly, the term "substituted napthylene" means a naphthylene group that is further substituted by halogen, hydroxy, protected hydroxy, $C_1$ to $C_{10}$ alkylthio, $C_1$ to $C_{10}$ alkylsulfoxide, $C_1$ to $C_{10}$ alkylsulfonyl, $C_1$ to $C_{10}$ substituted alkylthio, $C_1$ to $C_{10}$ substituted alkylsulfoxide, $C_1$ to $C_{10}$ substituted alkylsulfonyl, $C_1$ to $C_{12}$ alkyl, $C_1$ to $C_{12}$ alkoxy, $C_1$ to $C_{12}$ substituted alkyl, $C_1$ to $C_{12}$ alkoxy, oxo, protected oxo, (monosubstituted) amino, (disubstituted) amino, trifluoromethyl, carboxy, protected carboxy, phenyl, substituted phenyl, phenylthio, phenylsulfoxide, phenylsulfonyl, amino, or protected amino group.

The terms "halo" and "halogen" refer to the fluoro, chloro, bromo or iodo atoms. There can be one or more halogens, which are the same or different. Preferred halogens are chloro and fluoro.

The term "(monosubstituted)amino" refers to an amino group with one substituent chosen from the group consisting of phenyl, substituted phenyl, $C_1$ to $C_{12}$ alkyl, $C_1$ to $C_{12}$ substituted alkyl, $C_1$ to $C_{12}$ acyl, $C_1$ to $C_{12}$ substituted acyl, $C_2$ to $C_{12}$ alkenyl, $C_2$ to $C_{12}$ substituted alkenyl, $C_2$ to $C_{12}$ alkynyl, $C_2$ to $C_{12}$ substituted alkynyl, $C_7$ to $C_{18}$ phenylalkyl, $C_7$ to $C_{18}$ substituted phenylalkyl, heterocyclic ring, substituted heterocyclic ring, $C_1$ to $C_{12}$ heterocycloalkyl and $C_1$ to $C_{12}$ substituted heterocycloalkyl. The (monosubstituted)amino can additionally have an amino-protecting group as encompassed by the term "protected (monosubstituted)amino."

The term "(disubstituted)amino" refers to an amino group with two substituents chosen from the group consisting of phenyl, substituted phenyl, $C_1$ to $C_{12}$ alkyl, $C_1$ to $C_{12}$ substituted alkyl, $C_1$ to $C_{12}$ acyl, $C_2$ to $C_{12}$ alkenyl, $C_2$ to $C_{12}$ alkynyl, $C_7$ to $C_{18}$ phenylalkyl, $C_7$ to $C_{18}$ substituted phenylalkyl, $C_1$ to $C_{12}$ heterocycloalkyl and $C_1$ to $C_{12}$ substituted heterocycloalkyl. The two substituents can be the same or different.

The term "amino-protecting group" as used herein refers to substituents of the amino group commonly employed to block or protect the amino functionality while reacting other functional groups of the molecule. The term "protected (monosubstituted)amino" means there is an amino-protecting group on the monosubstituted amino nitrogen atom. In addition, the term "protected carboxamide" means there is an amino-protecting group on the carboxamide nitrogen. Similarly, the term "protected N—($C_1$ to $C_{12}$ alkyl)carboxamide" means there is an amino-protecting group on the carboxamide nitrogen.

Examples of such amino-protecting groups include the formyl ("For") group, the trityl group, the phthalimido group, the trichloroacetyl group, the chloroacetyl, bromoacetyl, and iodoacetyl groups, urethane-type blocking groups, such as t-butoxycarbonyl ("Boc"), 2-(4-biphenylyl)propyl-2-oxycarbonyl ("Bpoc"), 2-phenylpropyl-2-oxycarbonyl ("Poc"), 2-(4-xenyl)isopropoxycarbonyl, 1,1-diphenylethyl-1-oxycarbonyl, 1,1-diphenylpropyl-1-oxycarbonyl, 2-(3,5-dimethoxyphenyl)propyl-2-oxycarbonyl ("Ddz"), 2-(p-toluyl)propyl-2-oxycarbonyl, cyclopentanyloxycarbonyl, 1-methylcyclopentanyloxycarbonyl, cyclohexanyloxy-carbonyl, 1-methylcyclohexanyloxycarbonyl, 2-methylcyclohexanyloxycarbonyl, 2-(4-toluylsulfonyl)-ethoxycarbonyl, 2-(methylsulfonyl)ethoxycarbonyl, 2-(triphenylphosphino)-ethoxycarbonyl, 9-fluorenylmethoxycarbonyl ("Fmoc"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, isobornyloxycarbonyl, 1-piperidyloxycarbonyl, benzyloxycarbonyl ("Cbz"), 4-phenylbenzyloxycarbonyl, 2-methylbenzyloxy-carbonyl, -2,4,5,-tetramethylbenzyloxycarbonyl ("Tmz"), 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyl-oxycarbonyl, 4-bromobenzyloxycarbonyl, 3-bromobenzyloxycarbonyl, 4-nitrobenzyloxycarbonyl, 4-cyanobenzyloxycarbonyl, 4-(decyloxy)benzyloxycarbonyl and the like; the benzoylmethylsulfonyl group, dithiasuccinoyl ("Dts"), the 2-(nitro)phenylsulfenyl group ("Nps"), the diphenyl-phosphine oxide group and like amino-protecting groups. The species of amino-protecting group employed is not critical so long as the derivatized amino group is stable to the conditions of the subsequent reaction(s) and can be removed at the appropriate point without disrupting the remainder of the compounds. Preferred amino-protecting groups are Boc, Cbz and Fmoc. Further examples of amino-protecting groups embraced by the above term are well known in organic synthesis and the peptide art and are described by, for example, T. W. Greene and P. G. M. Wuts, "Protective Groups in Organic Synthesis," 2nd ed., John Wiley and Sons, New York, N.Y., 1991, Chapter 7, M. Bodanzsky, "Principles of Peptide Synthesis," 1st and 2nd revised ed., Springer-Verlag, New York, N.Y., 1984 and 1993, and Stewart and Young, "Solid Phase Peptide Synthesis," 2nd ed., Pierce Chemical Co., Rockford, Ill., 1984, each of which is incorporated herein by reference. The related term "protected amino" defines an amino group substituted with an amino-protecting group discussed above.

The term "protected guanidino" as used herein refers to an "amino-protecting group" on one or two of the guanidino nitrogen atoms. Examples of "protected guanidino" groups are described by T. W. Greene and P. G. M. Wuts; M. Bodanzsky; and Stewart and Young, supra.

The term "carboxy-protecting group" as used herein refers to one of the ester derivatives of the carboxylic acid group commonly employed to block or protect the carboxylic acid group while reactions are carried out on other functional groups on the compound. Examples of such carboxylic acid protecting groups include t-butyl, 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxytrityl, 4,4',4"-trimethoxytrityl, 2-phenylpropyl, trimethylsilyl, t-butyldimethylsilyl, phenacyl, 2,2,2-trichloroethyl, -(trimethylsilyl)ethyl, -(di(n-butyl)methylsilyl)ethyl, p-toluenesulfonylethyl, 4-nitrobenzylsulfonylethyl, allyl, cinnamyl, 1-(trimethylsilylmethyl)-propenyl and like moieties. The pecies of carboxy-protecting group employed is not critical so long as the derivatized carboxylic acid is stable to the conditions of subsequent reaction(s) and can be removed at the appropriate point without disrupting the remainder of the molecule. Further examples of these groups are found in E. Haslam, "Protective Groups in Organic Chemistry," J. G. W. McOmie, Ed., Plenum Press, New York, N.Y., 1973, Chapter 5, and T. W. Greene and P. G. M. Wuts, "Protective Groups in Organic Synthesis," 2nd ed., John Wiley and Sons, New York, N.Y., 1991, Chapter 5, each of which is incorporated herein by reference. A related term is "protected carboxy," which refers to a carboxy group substituted with one of the above carboxy-protecting groups.

The term "hydroxy-protecting group" refers to readily cleavable groups bonded to hydroxyl groups, such as the tetrahydropyranyl, 2-methoxypropyl, 1-ethoxyethyl, methoxymethyl, 2-methoxyethoxymethyl, methylthiomethyl, t-butyl, t-amyl, trityl, 4-methoxytrityl, 4,4'-dimethoxytrityl, 4,4',4"-trimethoxytrityl, benzyl, allyl, trimethylsilyl, (t-butyl)dimethylsilyl, 2,2,2-trichloroethoxycarbonyl groups and the like. The species of hydroxy-protecting groups is not critical so long as the derivatized hydroxyl group is stable to the conditions of subsequent reaction(s) and can be removed at the appropriate point without disrupting the remainder of the molecule. Further examples of hydroxy-protecting groups are described by C. B. Reese and E. Haslam, "Protective Groups in Organic Chemistry," J. G. W. McOmie, Ed., Plenum Press, New York, N.Y., 1973, Chapters 3 and 4, respectively, and T. W. Greene and P. G. M. Wuts, "Protective Groups in Organic Synthesis," 2nd ed., John Wiley and Sons, New York, N.Y., 1991, Chapters 2 and 3. Related terms are "protected hydroxy," and "protected hydroxymethyl" which refer to a hydroxy or hydroxymethyl substituted with one of the above hydroxy-protecting groups.

The term "$C_1$ to $C_{10}$ alkylthio" refers to sulfide groups such as methylthio, ethylthio, n-propylthio, isopropylthio, n-butylthio, t-butylthio and like groups.

The term "$C_1$ to $C_{10}$ alkylsulfoxide" indicates sulfoxide groups such as methylsulfoxide, ethylsulfoxide, n-propylsulfoxide, isopropylsulfoxide, n-butylsulfoxide, sec-butylsulfoxide and the like. The term "$C_1$ to $C_{10}$ alkylsulfonyl" encompasses groups such as methylsulfonyl, ethylsulfonyl, n-propylsulfonyl, isopropylsulfonyl, n-butylsulfonyl, t-butylsulfonyl and the like it should also be understood that the above thio, sulfoxide or sulfonyl groups can be at any point on the alkyl chain (e.g., 2-methylmercaptoethyl).

The terms "$C_1$ to $C_{10}$ substituted alkylthio," "$C_1$ to $C_{10}$ substituted alkylsulfoxide," and "$C_1$ to $C_{10}$ substituted alkylsulfonyl," denote the $C_1$ to $C_{10}$ alkyl portion of these groups may be substituted as described above in relation to "substituted alkyl."

The terms "phenylthio," "phenylsulfoxide," and "phenylsulfonyl" specify a thiol, a sulfoxide, or sulfone, respectively, containing a phenyl group. The terms "substituted phenylthio," "substituted phenylsulfoxide," and "substituted phenylsulfonyl" means that the phenyl of these groups can be substituted as described above in relation to "substituted phenyl."

The term "$C_1$ to $C_{12}$ alkylaminocarbonyl" means a $C_1$ to $C_{12}$ alkyl attached to a nitrogen of the aminocarbonyl group. Examples of $C_1$ to $C_{12}$ alkylaminocarbonyl include methylaminocarbonyl, ethylaminocarbonyl, propylaminocarbonyl and butylaminocarbonyl. The term "$C_1$ to $C_{12}$ substituted alkylaminocarbonyl" denotes a substituted alkyl bonded to a nitrogen of the aminocarbonyl group, which alkyl may be substituted as described above in relation to $C_1$ to $C_{12}$ substituted alkyl. Examples of $C_1$ to $C_{12}$ substituted alkylaminocarbonyl include, for example, methoxymethylaminocarbonyl, 2-chloroethylaminocarbonyl, 2-oxopropylaminocarbonyl and 4-phenylbutylaminocarbonyl.

The term "$C_1$ to $C_{12}$ alkoxycarbonyl" means a "$C_1$ to $C_{12}$ alkoxy" group attached to a carbonyl group. The term "$C_1$ to $C_{12}$ substituted alkoxycarbonyl" denotes a substituted alkoxy bonded to the carbonyl group, which alkoxy may be substituted as described above in relation to "$C_1$ to $C_{12}$ substituted alkyl."

The term "phenylaminocarbonyl" means a phenyl attached to a nitrogen of the aminocarbonyl group. The term "substituted phenylaminocarbonyl" denotes a substituted phenyl bonded to a nitrogen of the aminocarbonyl group, which phenyl may be substituted as described above in relation to substituted phenyl. Examples of substituted phenylaminocarbonyl include 2-chlorophenylaminocarbonyl, 3-chlorophenylaminocarbonyl 2-nitorphenylaminocarbonyl, 4-biphenylaminocarbonyl, and 4-methoxyphenylaminocarbonyl.

The term "$C_1$ to $C_{12}$ alkylaminothiocarbonyl" means a $C_1$ to $C_{12}$ alkyl attached to an aminothiocarbonyl group, wherein the alkyl has the same meaning as defined above. Examples of $C_1$ to $C_{12}$ alkylaminothiocarbonyl include methylaminothiocarbonyl, ethylaminothiocarbonyl, propylaminothiocarbonyl and butylaminothiocarbonyl.

The term "$C_1$ to $C_{12}$ substituted alkylaminothiocarbonyl" denotes a substituted alkyl bonded to an aminothiocarbonyl group, wherein the alkyl may be substituted as described above in relation to $C_1$ to $C_{12}$ substituted alkyl. Examples of $C_1$ to $C_{12}$ substituted alkylaminothiocarbonyl include, for example, methoxymethylaminothiocarbonyl, 2-chloroethylaminothiocarbonyl, 2-oxopropylaminothiocarbonyl and 4-phenylbutylaminothiocarbonyl.

The term "phenylaminothiocarbonyl" means a phenyl attached to an aminothiocarbonyl group, wherein the phenyl has the same meaning as defined above.

The term "substituted phenylaminothiocarbonyl" denotes a substituted phenyl bonded to an aminothiocarbonyl group, wherein phenyl may be substituted as described above in relation to substituted phenyl. Examples of substituted phenylaminothiocarbonyls include 2-chlorophenylaminothiocarbonyl, 3-chlorophenylaminothiocarbonyl, 2nitorphenylaminothiocarbonyl, 4-biphenylaminothiocarbonyl and 4-methoxyphenylaminothiocarbonyl.

The term "phenylene" means a phenyl group where the phenyl radical is bonded at two positions connecting together two separate additional groups. Examples of "phenylene" include 1,2-phenylene, 1,3-phenylene, and 1,4-phenylene.

The term "substituted phenylene" means a phenyl group where the phenyl radical is bonded at two positions connecting together two separate additional groups, wherein the phenyl is substituted as described above in relation to "substituted phenyl."

The term "substituted $C_1$ to $C_{12}$ alkylene" means a $C_1$ to $C_{12}$ alkyl group where the alkyl radical is bonded at two positions connecting together two separate additional groups and further bearing an additional substituent. Examples of "substituted $C_1$ to $C_{12}$ alkylene" includes aminomethylene, 1-(amino)-1,2-ethyl, 2-(amino)-1,2-ethyl, 1-(acetamido)-1, 2-ethyl, 2-(acetamido)-1,2-ethyl, 2-hydroxy-1,1-ethyl, 1-(amino)-1,3-propyl.

The terms "cyclic $C_2$ to $C_7$ alkylene," "substituted cyclic $C_2$ to $C_7$ alkylene," "cyclic $C_3$ to $C_7$ alkylene," "substituted cyclic $C_3$ to $C_7$ alkylene," "cyclic $C_2$ to $C_7$ heteroalkylene," and "substituted cyclic $C_2$ to $C_7$ heteroalkylene," defines such a cyclic group bonded ("fused") to the phenyl radical resulting in a bicyclic ring system. The cyclic group may be saturated or contain one or two double bonds. Furthermore, the cyclic group may have one or two methylene or methine groups replaced by one or two oxygen, nitrogen or sulfur atoms which are the cyclic $C_2$ to $C_7$ heteroalkylene.

The cyclic alkylene or heteroalkylene group may be substituted once or twice by the same or different substituents which, if appropriate, can be connected to another part of the compound (e.g., alkylene) selected from the group consisting of the following moieties: hydroxy, protected hydroxy, carboxy, protected carboxy, oxo, protected oxo, $C_1$ to $C_4$ acyloxy, formyl, $C_1$ to $C_{12}$ acyl, $C_1$ to $C_{12}$ alkyl, $C_1$ to $C_7$ alkoxy, $C_1$ to $C_{10}$ alkylthio, $C_1$ to $C_{10}$ alkylsulfoxide, $C_1$ to $C_{10}$ alkylsulfonyl, halo, amino, protected amino, (monosubstituted)amino, protected (monosubstituted) amino, (disubstituted)amino, hydroxymethyl or a protected hydroxymethyl.

The cyclic alkylene or heteroalkylene group fused onto the benzene radical can contain two to ten ring members, but it preferably contains three to six members. Examples of such saturated cyclic groups are when the resultant bicyclic ring system is 2,3-dihydro-indanyl and a tetralin ring. When the cyclic groups are unsaturated, examples occur when the resultant bicyclic ring system is a naphthyl ring or indolyl. Examples of fused cyclic groups which each contain one nitrogen atom and one or more double bond, preferably one or two double bonds, are when the benzene radical is fused to a pyridino, pyrano, pyrrolo, pyridinyl, dihydropyrrolo, or dihydropyridinyl ring. Examples of fused cyclic groups which each contain one oxygen atom and one or two double bonds are when the benzene radical ring is fused to a furo, pyrano, dihydrofurano, or dihydropyrano ring. Examples of fused cyclic groups which each have one sulfur atom and contain one or two double bonds are when the benzene radical is fused to a thieno, thiopyrano, dihydrothieno or dihydrothiopyrano ring. Examples of cyclic groups which contain two heteroatoms selected from sulfur and nitrogen and one or two double bonds are when the benzene radical ring is fused to a thiazolo, isothiazolo, dihydrothiazolo or dihydroisothiazolo ring. Examples of cyclic groups which contain two heteroatoms selected from oxygen and nitrogen and one or two double bonds are when the benzene ring is fused to an oxazolo, isoxazolo, dihydrooxazolo or dihydroisoxazolo ring. Examples of cyclic groups which contain two nitrogen heteroatoms and one or two double bonds occur when the benzene ring is fused to a pyrazolo, imidazolo, dihydropyrazolo or dihydroimidazolo ring or pyrazinyl.

The term "carbamoyl" means an —NCO— group where the radical is bonded at two positions connecting two separate additional groups.

One or more of the compounds of the invention, even within a given library, may be present as a salt. The term "salt" encompasses those salts that form with the carboxylate anions and amine nitrogens and include salts formed with the organic and inorganic anions and cations discussed below. Furthermore, the term includes salts that form by standard acid-base reactions with basic groups (such as amino groups) and organic or inorganic acids. Such acids include hydrochloric, hydrofluoric, trifluoroacetic, sulfuric, phosphoric, acetic, succinic, citric, lactic, maleic, fumaric, palmitic, cholic, pamoic, mucic, D-glutamic, D-camphoric, glutaric, phthalic, tartaric, lauric, stearic, salicyclic, methanesulfonic, benzenesulfonic, sorbic, picric, benzoic, cinnamic, and like acids.

The term "organic or inorganic cation" refers to counter-ions for the carboxylate anion of a carboxylate salt. The counter-ions are chosen from the alkali and alkaline earth metals, (such as lithium, sodium, potassium, barium, aluminum and calcium); ammonium and mono-, di- and tri-alkyl amines such as trimethylamine, cyclohexylamine; and the organic cations, such as dibenzylammonium, benzylammonium, 2-hydroxyethylammonium, bis(2-hydroxyethyl)ammonium, phenylethylbenzylammonium, dibenzylethylenediammonium, and like cations. See, for example, "Pharmaceutical Salts," Berge et al., J. Pharm. Sci., 66:1–19 (1977), which is incorporated herein by reference. Other cations encompassed by the above term include the protonated form of procaine, quinine and N-ethylglucosamine, and the protonated forms of basic amino acids such as glycine, ornithine, histidine, phenylglycine, lysine and arginine. Furthermore, any zwitterionic form of the instant compounds formed by a carboxylic acid and an amino group is referred to by this term. For example, a cation for a carboxylate anion will exist when a position is substituted with a (quaternary ammonium)methyl group. A preferred cation for the carboxylate anion is the sodium cation.

The compounds of the invention can also exist as solvates and hydrates. Thus, these compounds may crystallize with, for example, waters of hydration, or one, a number of, or any fraction thereof of molecules of the mother liquor solvent. The solvates and hydrates of such compounds are included within the scope of this invention.

One or more compounds of the invention, even when in a library, can be in the biologically active ester form, such as the non-toxic, metabolically-labile ester-form. Such ester forms induce increased blood levels and prolong the efficacy of the corresponding non-esterified forms of the compounds. Ester groups which can be used include the lower alkoxymethyl groups, for example, methoxymethyl, ethoxymethyl, isopropoxymethyl and the like; the —($C_1$ to $C_{12}$) alkoxyethyl groups, for example methoxyethyl, ethoxyethyl, propoxyethyl, isopropoxyethyl and the like; the 2-oxo-1,3-diooxlen-4-ylmethyl groups, such as 5-methyl-2-oxo-1,3-dioxolen-4-ylmethyl, 5-phenyl-2-oxo-1,3-dioxolen-4-ylmethyl and the like; the $C_1$ to $C_{10}$ alkylthiomethyl groups, for example methylthiomethyl, ethylthiomethyl, isopropylthiomethyl and the like; the acyloxymethyl groups, for example pivaloyloxymethyl, pivaloyloxyethyl, -acetoxymethyl and the like; the ethoxycarbonyl-1-methyl group; the -acetoxyethyl; the 1-($C_1$ to $C_{12}$ alkyloxycarbonyloxy)ethyl groups such as the 1-(ethoxycarbonyloxy)ethyl group; and the 1-($C_1$ to $C_{12}$ alkylaminocarbonyloxy)ethyl groups such as the 1-(methylaminocarbonyloxy)ethyl group.

The term "amino acid" includes any one of the twenty naturally-occurring amino acids or the D-form of any one of the naturally-occurring amino acids. In addition, the term "amino acid" also includes other non-naturally occurring amino acids besides the D-amino acids, which are functional equivalents of the naturally-occurring amino acids. Such non-naturally-occurring amino acids include, for example, norleucine ("Nle"), norvaline ("Nva"), L- or D-naphthalanine, ornithine ("Orn"), homoarginine (homoArg) and others well known in the peptide art, such as those described in M. Bodanzsky, "Principles of Peptide Synthesis," 1st and 2nd revised ed., Springer-Verlag, New York, N.Y., 1984 and 1993, and Stewart and Young, "Solid Phase Peptide Synthesis," 2nd ed., Pierce Chemical Co., Rockford, Ill., 1984, both of which are incorporated herein by reference. Amino acids and amino acid analogs can be purchased commercially (Sigma Chemical Co.; Advanced Chemtech) or synthesized using methods known in the art.

The term "functionalized resin" means any resin, crosslinked or otherwise, where functional groups have been introduced into the resin, as is common in the art. Such resins include, for example, those functionalized with amino, alkylhalo, formyl or hydroxy groups. Such resins which can serve as solid supports are well known in the art and include, for example, 4-methylbenzhydrylamine-copoly (styrene-1% divinylbenzene) (MBHA), 4-hydroxymethylphenoxymethyl-copoly(styrene-1% divinylbenzene), 4-oxymethyl-phenyl-acetamido-copoly (stryene-1% divinylbenzene)(Wang), 4-(oxymethyl)-phenylacetamido methyl (Pam), and Tentagel™, from Rapp Polymere Gmbh, trialkoxy-diphenyl-methyl ester-copoly (styrene-1% divinylbenzene)(RINK) all of which are commercially available. Other functionalized resins are known in the art and can be use without departure from the scope of the current invention. Such resins may include those described in Jung, G., Combinatorial Peptide and Nonpeptide Libraries, A Handbook (VCH Verlag, 1996) or Bunin, B. A., The Combinatorial Index (Academic Press, 1998) and are incorporated herein by reference.

As used herein, a "combinatorial library" is an intentionally created collection of differing molecules which can be prepared by the means provided below or otherwise and screened for biological activity in a variety of formats (e.g., libraries of soluble molecules, libraries of compounds attached to resin beads, silica chips or other solid supports). A "combinatorial library," as defined above, involves successive rounds of chemical syntheses based on a common starting structure. The combinatorial libraries can be screened in any variety of assays, such as those detailed below as well as others useful for assessing their biological activity. The combinatorial libraries will generally have at least one active compound and are generally prepared such that the compounds are in equimolar quantities.

Compounds disclosed in previous work that are not disclosed as part of a collection of compounds or not disclosed as intended for use as part of such a collection are not part of a "combinatorial library" of the invention. In addition, compounds that are in an unintentional or undesired mixture are not part of a "combinatorial library" of the invention.

A combinatorial library of the invention can contain two or more of the above-described compounds. The invention further provides a combinatorial library containing three, four or five or more of the above-described compounds. In another embodiment of the invention, a combinatorial library can contain ten or more of the above-described compounds. In yet another embodiment of the invention, a combinatorial library can contain fifty or more of the above-described compounds. If desired, a combinatorial library of the invention can contain 100,000 or more, or even 1,000,000 or more, of the above-described compounds.

By way of example, the preparation of the combinatorial libraries can use the "split resin approach." The split resin approach is described by, for example, U.S. Pat. No. 5,010,175 to Rutter, WO PCT 91/19735 to Simon, and Gallop et al., J. Med. Chem., 37:1233–1251 (1994), all of which are incorporated herein by reference.

The amino acids are indicated herein by either their full name or by the commonly known three letter code. Further, in the naming of amino acids, "D-" designates an amino acid having the "D" configuration, as opposed to the naturally occurring L-amino acids. Where no specific configuration is indicated, one skilled in the art would understand the amino acid to be an L-amino acid. The amino acids can, however, also be in racemic mixtures of the D- and L-configuration or the D-amino acid can readily be substituted for that in the L-configuration.

For preparing pharmaceutical compositions containing compounds of the invention, inert, pharmaceutically acceptable carriers are used. The pharmaceutical carrier can be either solid or liquid. Solid form preparations include, for example, powders, tablets, dispersible granules, capsules, cachets, and suppositories.

A solid carrier can be one or more substances which can also act as diluents, flavoring agents, solubilizers, lubricants, suspending agents, binders, or tablet disintegrating agents; it can also be an encapsulating material.

In powders, the carrier is generally a finely divided solid which is in a mixture with the finely divided active component. In tablets, the active compound is mixed with the carrier having the necessary binding properties in suitable proportions and compacted in the shape and size desired.

For preparing pharmaceutical composition in the form of suppositories, a low-melting wax such as a mixture of fatty acid glycerides and cocoa butter is first melted and the active ingredient is dispersed therein by, for example, stirring. The molten homogeneous mixture is then poured into convenient-sized molds and allowed to cool and solidify.

Powders and tablets preferably contain between about 5% to about 70% by weight of the active ingredient. Suitable carriers include, for example, magnesium carbonate, magnesium stearate, talc, lactose, sugar, pectin, dextrin, starch, tragacanth, methyl cellulose, sodium carboxymethyl cellulose, a low-melting wax, cocoa butter and the like.

The pharmaceutical compositions can include the formulation of the active compound with encapsulating material as a carrier providing a capsule in which the active component (with or without other carriers) is surrounded by a carrier, which is thus in association with it. In a similar manner, cachets are also included. Tablets, powders, cachets, and capsules can be used as solid dosage forms suitable for oral administration.

Liquid pharmaceutical compositions include, for example, solutions suitable for oral or parenteral administration, or suspensions, and emulsions suitable for oral administration. Sterile water solutions of the active component or sterile solutions of the active component in solvents comprising water, ethanol, or propylene glycol are examples of liquid compositions suitable for parenteral administration.

Sterile solutions can be prepared by dissolving the active component in the desired solvent system, and then passing the resulting solution through a membrane filter to sterilize it or, alternatively, by dissolving the sterile compound in a previously sterilized solvent under sterile conditions.

Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethyl cellulose, and other suspending agents known to the pharmaceutical formulation art.

Preferably, the pharmaceutical composition is in unit dosage form. In such form, the composition is divided into unit doses containing appropriate quantities of the active pyridine carboxamide or sulfonamide compound. The unit dosage form can be a packaged preparation, the package containing discrete quantities of the preparation, for example, packeted tablets, capsules, and powders in vials or ampules. The unit dosage form can also be a capsule, cachet, or tablet itself, or it can be the appropriate number of any of these packaged forms.

As pharmaceutical compositions for treating infections, pain, or any other indication the compounds of the present invention are generally in a pharmaceutical composition so as to be administered to a subject at dosage levels of from 0.7 to 7000 mg per day, and preferably 1 to 500 mg per day, for a normal human adult of approximately 70 kg of body weight, this translates into a dosage of from 0.01 to 100 mg/kg of body weight per day. The specific dosages employed, however, can be varied depending upon the requirements of the patient, the severity of the condition being treated, and the activity of the compound being employed. The determination of optimum dosages for a particular situation is within the skill of the art.

The compounds and combinatorial libraries of the invention can be prepared as set forth in FIG. 1 and as described below.

Variant pyridine carboxamide or sulfonamide derivative compounds and combinatorial libraries can be prepared in order to achieve a high level of diversity. For instance, Merrifield resin can be reacted with ammonia or a primary amine (variable—$NH_2$), resulting in phenylene—$CH_2$—NH-variable attached to resin (see FIG. 1).

Alternatively, a bromo-Wang resin can be prepared and reacted with in the same manner as the Merrifield resin described above. See Ngu et al., *Tetr. Lett.*, 38:973–976 (1997), which is incorporated herein by reference. In addition, MBHA resin can be reacted with an alkyl halide to produce a methylbenzhydryl—$CH_2$—NH-variable or MBHA resin can be reacted with an aldehyde followed by reduction to produce a methylbenzhydryl—$CH_2$—NH-variable.

Moreover, secondary amines can be attached to resin. For example, an N-alkyl amino acid such as Me—NH—C(O)—OH can be attached to resin through an ester linkage. Alternatively, a cyclic diimine such as piperazine can be attached to resin through a ring nitrogen methyl linkage, or a diamine such as N,N'-dimethykethyelenediamine can be attached through a similar linkage. As another example, an alcohol amine such as N-methylethanolamine can be attached to resin through an ether linkage.

The resin-attached amine can then be coupled to a substituted pyridine, for example, 6-chloronicotinic acid, resulting in a pyridine that is substituted with a halo and is also substituted with a substituted carboxamide containing the group —C(O)—N(variable)- at para positions, wherein the carboxamide carbon is directly attached to the pyridine ring (see FIG. 1). There are many 6-halopyridines available commercially. Moreover, pyridinones can be made via modified Hantzsch pyridine synthesis, from which 6-halopyridines can be derived in one step.

It should be understood that the carboxylic acid substitution can be any of the other unoccupied positions of the pyridine ring. Moreover, the pyridine ring can be further substituted, for example, with an alkyl or substituted alkyl.

It should also be understood that the subject invention encompasses coupling the resin-attached amine with a pyridine substituted with a sulfonyl group instead of a caroxyl group, resulting in a substituted sulfonamide containing the group —$S(O_2)$—N(variable)-, wherein the sulfur atom is directly attached to the pyridine ring.

The halo group can then be displaced by a diamine of the formula amino-variable-amino, resulting in a substitution of the formula NH-variable-amino at the position previously occupied by the halo and also substituted with a substituted carboxamide group or sulfonamide containing, respectively, the group —C(O)—N(variable)- or the group —$S(O_2)$—N(variable)- at one of the other positions of the pyridine ring.

Alternatively, the halo group can be displaced by (i) a amino compound attached to a non-aromatic heterocycle or substituted heterocycle having at least one ring nitrogen atom; (ii) a non-aromatic heterocycle or substituted heterocycle having at least two ring nitrogen atoms; or (iii) a bicyclic non-aromatic heterocycle or substituted heterocycle, each heterocycle or substituted heterocycle having at least one ring nitrogen atom.

Moreover, the resulting terminal amino or imino group of the pyridine can be reacted with a carboxylic acid of the formula variable—COOH, resulting in the substitution containing the group of the formula —NH-variable—NH—C(O)-variable (see FIG. 1) or the formula ring nitrogen-variable—NH—C(O)-variable at that position of the pyridine ring.

Resin-bound pyridine carboxamide or sulfonamide derivative compounds can be cleaved by treating them, for example, with HF gas. The compounds can be extracted from the spent resin, for example, with AcOH.

Pyridine carboxamide or sulfonamide derivative compounds and libraries, such as those of the present invention, can be made utilizing individual polypropylene bags, referred to as "tea bags" (see Houghten et al., *Proc. Natl. Acad. Sci. USA* 82: 5131 (1985); *Biochemistry*, 32:11035 (1993); and U.S. Pat. No. 4,631,211, all of which are incorporated herein by reference).

The nonsupport-bound combinatorial libraries can be screened as single compounds. In addition, the nonsupport-bound combinatorial libraries can be screened as mixtures in solution in assays such as radio-receptor inhibition assays, anti-bacterial assays, anti-fungal assays, calmodulin-dependent phosphodiesterase (CaMPDE) assays and phosphodiesterase (PDE) assays, as described in detail below. Deconvolution of highly active mixtures can then be carried out by iterative or positional scanning methods. These techniques, the iterative approach or the positional scanning approach, can be utilized for finding other active compounds within the combinatorial libraries of the present invention using any one of the below-described assays or others well known in the art.

The iterative approach is well-known and is set forth in general in Houghten et al., *Nature*, 354, 84–86 (1991) and Dooley et al., *Science*, 266, 2019–2022 (1994), both of which are incorporated herein by reference. In the iterative approach, for example, sub-libraries of a molecule having three variable groups are made wherein the first variable is defined. Each of the compounds with the defined variable group is reacted with all of the other possibilities at the other two variable groups. These sub-libraries are each tested to define the identity of the second variable in the sub-library having the highest activity in the screen of choice. A new sub-library with the first two variable positions defined is reacted again with all the other possibilities at the remaining undefined variable position. As before, the identity of the third variable position in the sub-library having the highest activity is determined. If more variables exist, this process is repeated for all variables, yielding the compound with each variable contributing to the highest desired activity in the screening process. Promising compounds from this process can then be synthesized on larger scale in traditional single-compound synthetic methods for further biological investigation.

The positional-scanning approach has been described for various combinatorial libraries as described, for example, in R. Houghten et al. PCT/US91/08694 and U.S. Pat. No. 5,556,762, both of which are incorporated herein by reference. In the positional scanning approach, sublibraries are made defining only one variable with each set of sublibraries and all possible sublibraries with each single variable defined (and all other possibilities at all of the other variable positions), made and tested. From the instant description one skilled in the art could synthesize combinatorial libraries wherein two fixed positions are defined at a time. From the testing of each single-variable defined combinatorial library, the optimum substituent at that position can be determined, pointing to the optimum or at least a series of compounds having a maximum of the desired biological activity. Thus, the number of sublibraries for compounds with a single position defined will be the number of different substituents desired at that position, and the number of all the compounds in each sublibrary will be the product of the number of substituents at each of the other variables.

Individual compounds and pharmaceutical compositions containing the compounds, as well as methods of using the same, are included within the scope of the present invention. The compounds of the present invention can be used for a variety of purposes and indications and as medicaments for any such purposes and indications. For example, pyridine carboxamide or sulfonamide derivative compounds of the present invention can be used as pesticides, acaricides, receptor agonists or antagonists and antimicrobial agents, including antibacterial or antiviral agents. The libraries can be screened in any variety of melanocortin receptor and related activity assays, such as those detailed below as well as others known in the art. Additionally, the subject compounds can be useful as analgesics. Assays which can be used to test the biological activity of the instant compounds include antimicrobial assays, a competitive enzyme-linked immunoabsorbent assay and radio-receptor assays, as described below.

The melanocortin (MC) receptors are a group of cell surface proteins that mediate a variety of physiological effects, including regulation of adrenal gland function such as production of the glucocorticoids cortisol and aldosterone; control of melanocyte growth and pigment production; thermoregulation; immunomodulation; and analgesia. Five distinct MC receptors have been cloned and are expressed in a variety of tissues, including melanocytes, adrenal cortex, brain, gut, placenta, skeletal muscle, lung, spleen, thymus, bone marrow, pituitary, gonads and adipose tissue (Tatro, *Neuroimmunomodulation* 3:259–284 (1996)). Three MC receptors, MCR-1, MCR-3 and MCR-4, are expressed in brain tissue (Xia et al., *Neuroreport* 6:2193–2196 (1995)).

A variety of ligands termed melanocortins function as agonists that stimulate the activity of MC receptors. The melanocortins include melanocyte-stimulating hormones (MSH) such as α-MSH, β-MSH and γ-MSH, as well as adrenocorticotropic hormone (ACTH). Individual ligands can bind to multiple MC receptors with differing relative affinities. The variety of ligands and MC receptors with differential tissue-specific expression likely provides the molecular basis for the diverse physiological effects of melanocortins and MC receptors. For example, α-MSH antagonizes the actions of immunological substances such as cytokines and acts to modulate fever, inflammation and immune responses (Catania and Lipton, *Annals N. Y. Acad. Sci.* 680:412–423 (1993)).

The role of certain specific MC receptors in some of the physiological effects described above for MC receptors has been elucidated. For example, MCR-1 is involved in pain and inflammation. MCR-1 mRNA is expressed in neutrophils (Catania et al., *Peptides* 17:675–679 (1996)). The anti-inflammatory agent α-MSH was found to inhibit migration of neutrophils. Thus, the presence of MCR-1 in neutrophils correlates with the anti-inflammatory activity of α-MSH.

An interesting link of MC receptors to regulation of food intake and obesity has recently been described. The brain MC receptor MCR-4 has been shown to function in the regulation of body weight and food intake. Mice in which MCR-4 has been knocked out exhibit weight gain (Huszar et al., *Cell* 88:131–141 (1997)). In addition, injection into brain of synthetic peptides that mimic melanocortins and bind to MCR-4 caused suppressed feeding in normal and mutant obese mice (Fan et al., *Nature* 385:165–168 (1997)). These results indicate that the brain MC receptor MCR-4 functions in regulating food intake and body weight.

Due to the varied physiological activities of MC receptors, high affinity ligands of MC receptors could be used to exploit the varied physiological responses of MC receptors by functioning as potential therapeutic agents or as lead compounds for the development of therapeutic agents. Furthermore, due to the effect of MC receptors on the activity of various cytokines, high affinity MC receptor ligands could also be used to regulate cytokine activity.

A variety of assays can be used to identify or characterize MC receptor ligands of the invention. For example, the ability of a pyridine carboxamide or sulfonamide derivative compound to compete for binding of a known MC receptor ligand can be used to assess the affinity and specificity of a pyridine carboxamide or sulfonamide compound for one or more MC receptors. Any MC receptor ligand can be used so long as the ligand can be labeled with a detectable moiety. The detectable moiety can be, for example, a radiolabel, fluorescent label or chromophore, or any detectable functional moiety so long as the MC receptor ligand exhibits specific MC receptor binding. A particularly useful detectable MC receptor ligand for identifying and characterizing other MC receptor ligands is $^{125}$I-HP 467, which has the amino acid sequence Ac-Nle-Gln-His- (p(I)-D-Phe)-Arg-(D-Trp)-Gly-NH$_2$ and is described in Dooley et al., "Melanocortin Receptor Ligands and Methods of Using Same," U.S. patent application Ser. No. 09/027,108, filed Feb. 20, 1998, which is incorporated herein by reference. HP 467 is a paraiodinated form of HP 228.

Using assay methods such as those described above, binding kinetics and competition with radiolabeled HP 467 can confirm that pyridine carboxamide or sulfonamide compounds of the invention bind to one or more MC receptors. Furthermore, pyridine carboxamide or sulfonamide derivative compounds of the invention can exhibit a range of affinities and specificity for various MC receptors.

The invention provides MC receptor ligands that can bind to several MC receptors with similar affinity. In addition, the invention also provides MC receptor ligands that can be selective for one or more MC receptors. As used herein, the term "selective" means that the affinity of a MC receptor ligand differs between one MC receptor and another by about 10-fold, generally about 20- to 50-fold, and particularly about 100-fold. In some cases, a MC receptor ligand having broad specificity is desired. In other cases, it is desirable to use MC receptor ligands having selectivity for a particular MC receptor. For example, MCR-1 ligands are particularly useful for treating pain and inflammation, whereas NCR-4 ligands are useful for treating obesity. The binding characteristics and specificity of a given MC receptor ligand can be selected based on the particular disease or physiological effect that is desired to be altered.

Another assay useful for identifying or characterizing MC receptor ligands measures signaling of MC receptors. MC receptors are G protein-coupled receptors that couple to adenylate cyclase and produce cAMP. Therefore, measuring cAMP production in a cell expressing a MC receptor and treated with a MC receptor ligand can be used to assess the function of the MC receptor ligand in activating a MC receptor.

Ligands for MC-3 that can alter the activity of an MC-3 receptor can be useful for treating sexual dysfunction and other conditions or conditions associated with MC-3 such as inflammation. Other MC-3-associated conditions that can be treated with the MC-3 receptor ligands include disuse deconditioning; organ damage such as organ transplantation or ischemic injury; adverse reactions associated with cancer chemotherapy; diseases such as atherosclerosis that are mediated by free radicals and nitric oxide action; bacterial endotoxic sepsis and related shock; adult respiratory distress syndrome; and autoimmune or other patho-immunogenic diseases or reactions such as allergic reactions or anaphylaxis, rheumatoid arthritis, inflammatory bowel disease, ulcerative colitis, glomerulonephritis, systemic lupus erythematosus, transplant atherosclerosis and parasitic mediated immune dysfunctions such as Chagas's disease.

The invention further provides a method for treating an MC-3-associated condition in a subject. The term "MC-3-associated condition" includes any condition or condition mediated by MC-3 or can be affected by binding an MC-3 ligand. Such conditions include inflammation and sexual dysfunction.

The term "sexual dysfunction" herein means any condition that inhibits or impairs normal sexual function, including coitus. However, the term need not be limited to physiological conditions, but may include psychogenic conditions or perceived impairment without a formal diagnosis of pathology.

In males, sexual dysfunction includes erectile dysfunction. The term "erectile dysfunction" or "impotence" means herein the inability or impaired ability to attain or sustain an erection that would be of satisfactory rigidity for coitus. Sexual dysfunction in. males can also include premature ejaculation and priapism, which is a condition of prolonged and sometimes painful erection unrelated to sexual activity, often associated with sickle-cell disease.

In females, sexual dysfunction includes sexual arousal disorder. The term "sexual arousal disorder" means herein a persistent or recurrent failure to attain or maintain the lubrication-swelling response of sexual excitement until completion of sexual activity. Sexual dysfunction in females can also include inhibited orgasm and dyspareunia, which is painful or difficult coitus. Sexual dysfunction can also be manifested as inhibited sexual desire or inhibited lordosis behavior in animals.

In addition, the ability of the compounds to inhibit bacterial growth, and therefore be useful to that infection, can be determined by methods well known in the art. Compounds of the present invention were shown to have antimicrobial activity by the in vitro antimicrobial activity assay described below and, therefore, are useful as antimicrobial agents (see Example 16).

In addition, an exemplary in vitro antimicrobial activity assay is described in Blondelle and Houghten, *Biochemistry* 30:4671–4678 (1991), which is incorporated herein by reference. In brief, Staphylococcus aureus ATCC 29213 (Rockville, Md.) is grown overnight at 37° C. in Mueller-Hinton broth, then re-inoculated and incubated at 37° C. to reach the exponential phase of bacterial growth (i.e., a final bacterial suspension containing $10^5$ to $5 \times 10^5$ colony-forming units/ml). The concentration of cells is established by plating 100 $\mu$l of the culture solution using serial dilutions (e.g., $10^{-2}$, $10^{-3}$ and $10^{-4}$) onto solid agar plates. In 96-well tissue culture plates, compounds, individual or in mixtures, are added to the bacterial suspension at concentrations derived from serial two-fold dilutions ranging from 1500 to 2.9 $\mu$g/ml. The plates are incubated overnight at 37° C. and the growth determined at each concentration by $OD_{620}$ nm. The $IC_{50}$ (the concentration necessary to inhibit 50% of the growth of the bacteria) can then be calculated.

The competitive ELISA method which can be used here is a modification of the direct ELISA technique described previously in Appel et al., *J. Immunol.* 144:976–983 (1990), which is incorporated herein by reference. It differs only in the MAb addition step. Briefly, multi-well microplates are coated with the antigenic peptide (Ac-GASPYPNLSNQQT-NH$_2$) at a concentration of 100 pmol/50 $\mu$l. After blocking, 25 $\mu$l of a 1.0 mg/ml solution of each mixture of a synthetic combinatorial library (or individual compound) is added, followed by MAb 125-10F3 (Appel et al., supra) (25 $\mu$l per well). The MAb is added at a fixed dilution in which the bicyclic guanidine in solution effectively competes for MAb binding with the antigenic peptide adsorbed to the plate. The remaining steps are the same as for direct ELISA. The concentration of compound necessary to inhibit 50% of the MAb binding to the control peptide on the plate ($IC_{50}$) is determined by serial dilutions of the compound.

Alternative screening can be done with radio-receptor assays. The radio-receptor assay, can be selective for any one of the $\mu$, $\kappa$, or $\delta$ opiate receptors. Compounds of the present invention can be useful in vitro for the diagnosis of relevant opioid receptor subtypes, such as $\kappa$, in the brain and other tissue samples. Similarly, the compounds can be used in vivo diagnostically to localize opioid receptor subtypes.

The radio-receptor assays are also an indication of the compounds' analgesic properties as described, for example, in Dooley et al., *Proc. Natl. Acad. Sci.*, 90:10811–10815 (1993). For example, it can be envisioned that these compounds can be used for therapeutic purposes to block the peripheral effects of a centrally acting pain killer. For instance, morphine is a centrally acting pain killer. Morphine, however, has a number of deleterious effects in the periphery which are not required for the desired analgesic effects, such as constipation and pruritus (itching). While it is known that the many compounds do not readily cross the blood-brain barrier and, therefore, elicit no central effect, the subject compounds can have value in blocking the periphery effects of morphine, such as constipation and pruritus. Accordingly, the subject compounds can also be useful as drugs, namely as analgesics, or to treat pathologies associated with other compounds which interact with the opioid receptor system.

Additionally, such compounds can be tested in a $\sigma$ receptor assay. Ligands for the a receptor can be useful as antipsychotic agents, as described in Abou-Gharbia et al., *Annual Reports in Medicinal Chemistry*, 28:1–10 (1993)

Radio-receptor assays can be performed with particulate membranes prepared using a modification of the method described in Pasternak et al., *Mol. Pharmacol.* 11:340–351 (1975), which is incorporated herein by reference. Rat brains frozen in liquid nitrogen can be obtained from Rockland (Gilbertsville, Pa.). The brains are thawed, the cerebella removed and the remaining tissue weighed. Each brain is individually homogenized in 40 ml Tris-HCl buffer (50 mM, pH 7.4, 4° C.) and centrifuged (Sorvall® RC5C SA-600:Du Pont, Wilmington, Del.) (16,000 rpm) for 10 minutes. The pellets are resuspended in fresh Tris-HCl buffer and incubated at 37° C. for 40 minutes. Following incubation, the suspensions are centrifuged as before, the resulting pellets resuspended in 100 volumes of Tris buffer and the suspensions combined. Membrane suspensions are prepared and used in the same day. Protein content of the crude homogenates generally range from 0.15–0.2 mg/ml as determined using the method described in Bradford, M. M., *Anal. Biochem.* 72:248–254 (1976), which is incorporated herein by reference.

Binding assays are carried out in polypropylene tubes, each tube containing 0.5 ml of membrane suspension. 8 nM of $^3$H-[D-Ala$^2$,Me-Phe$^4$,Gly-ol$^5$]enkephalin (DAMGO) (specific activity=36 Ci/mmol, 160,000 cpm per tube; which can be obtained from Multiple Peptide Systems, San Diego, Calif., through NIDA drug distribution program 271-90-7302) and 80 $\mu$g/ml of bicyclic guanidine, individual or as a mixture and Tris-HCl buffer in a total volume of 0.65 ml. Assay tubes are incubated for 60 mins. at 25° C. The reaction is terminated by filtration through GF-B filters on a Tomtec harvester (Orange, Conn.). The filters are subsequently washed with 6 ml of Tris-HCl buffer, 4° C. Bound radioactivity is counted on a Pharmacia Biotech Betaplate Liquid Scintillation Counter (Piscataway, N.J.) and expressed in cpm. To determine inter- and intra-assay variation, standard curves in which $^3$H-DAMGO is incubated in the presence of a range of concentrations of unlabeled DAMGO (0.13–3900 nM) are generally included in each plate of each assay (a 96-well format). Competitive inhibition assays are performed as above using serial dilutions of the bicyclic guanidines, individually or in mixtures. IC$_{50}$ values (the concentration necessary to inhibit 50% of $^3$H-DAMGO binding) are then calculated. IC$_{50}$ values of less than 1000 nM are indicative of highly active opioid compounds which bind to the $\mu$ receptor, with particularly active compounds having IC$_{50}$ values of 100 nM or less and the most active compounds with values of less than 10 nM.

As opposed to this u receptor selective assay, which can be carried out using $^3$H-DAMGO as radioligand, as described above, assays selective for K receptors can be carried out using [$^3$H]-U69,593 (3 nM, specific activity 62 Ci/mmol) as radioligand. Assays selective for δ opiate receptors can be carried out using tritiated DSLET ([D-Ser$^2$, D-Leu$^5$]-threonine-enkephalin) as radioligand. Assays selective for the a opiate receptor can use radiolabeled pentazocine as ligand.

Screening of combinatorial libraries and compounds of the invention can be done with an anti-fungal assay. Compounds of the present invention can be useful for treating fungal infections.

Screening of combinatorial libraries and compounds of the invention also can be done with a calmodulin-dependent phosphodiesterase (CaMPDE) assay. Compounds of the present invention can be useful as calmodulin antagonists.

Calmodulin (CaM), which is the major intracellular calcium receptor, is involved in many processes that are crucial to cellular viability. In particular, calmodulin is implicated in calcium-stimulated cell proliferation. Calmodulin antagonists are, therefore, useful for treating conditions associated with increased cell proliferation, for example, cancer. In addition, calmodulin antagonists such as compounds of the subject invention are useful both in vitro and in vivo for identifying the role of calmodulin in other biological processes. The disadvantages of known antagonists such as trifluoperazine and N-(4-aminobutyl)-5-chloro-2-naphthalenesulfonamide (W13) include their non-specificity and toxicity. In contrast, advantages of the combinatorial libraries and compounds of the subject invention as calmodulin antagonists include their reduced flexibility and ability to generate broader conformational space of interactive residues as compared to their linear counterparts.

An example of an assay that identifies CaM antagonists is a CaMPDE assay. In brief, samples are mixed with 50 $\mu$l of assay buffer (360 mM Tris, 360 mM Imidazole, 45 mM Mg(CH$_3$COO)$_2$, pH 7.5) and 10 $\mu$l of CaCl$_2$ (4.5 mM) to a final volume of 251 $\mu$l. 25 $\mu$l of calmodulin stock solution (Boehringer Mannheim; 0.01 $\mu$g/$\mu$l) is then added and the samples then sit at room temperature for 10 minutes. 14 $\mu$l of PDE (Sigma; 2 Units dissolved in 4 ml of water; stock concentration: 0.0005 Units/$\mu$l) is then added, followed by 50 $\mu$l of 5'-nucleotidase (Sigma; 100 Units dissolved in 10 ml of 10 mM Tris-HCl containing 0.5 mM Mg(CH$_3$COO)$_2$, pH 7.0;stock concentration: 10 Units/ml) The samples are then incubated for 10 minutes at 30° C. 50 $\mu$l of adenosine 3',5'-cyclic monophosphate (cAMP) (20 mM in water at pH 7.0) is added, the samples incubated for 1 hour at 30° C. and then vortexed. 200 $\mu$l of trichloroacetic acid (TCA) (55% in water) is added to a 200 $\mu$l sample aliquot, which is then vortexed and centrifuged for 10 minutes. 80 $\mu$l of the resulting supernatants of each sample is transferred to a 96-well plate, with 2 wells each containing 80 $\mu$l of each sample. 80 $\mu$l of ammonium molybdate (1.1% in 1.1N H$_2$SO$_4$) is then added to all the wells, and the OD of each were determined at 730nm, with the values later subtracted to the final OD reading. 16 $\mu$l of reducing agent (6g sodium bisulfite, 0.6g sodium sulfite and 125mg of 1-amino-2-naphtol-4-sulfonic acid in 50 ml of water) is then added to one of each sample duplicate and 16 $\mu$l of water is added to the other duplicate. After sitting for 1 hour at room temperature, the OD of each well is determined at 730 nm. The percent inhibition of calmodulin activity is then calculated for each sample, using as 0% inhibition a control sample containing all reagents without any test samples and as 100% inhibition a control sample containing test samples and all reagents except calmodulin. In addition, the percent inhibition of phosphodiesterase activity was determined by following a similar protocol as the CaMPDE assay described above, except not adding calmodulin to the sample mixture and calculating the percent inhibition by using as 0% inhibition a control reagent without any test samples and as 100% inhibition a control sample containing test samples and all reagents except cAMP.

The following examples are provided to illustrate but not limit the present invention. In the examples, the following abreviations have the corresponding meanings:

MBHA: 4-methylbenzhydrylamine;
DMF: N,N-dimethylforamide;
HOBt: 1-hydroxybenzotriazole;
DMSO: dimethylsulfoxide;
Boc: tert-butoxycarbonyl;
FMOC: 9-fluorenyl-methoxycarbonyl;
DMAP: 4-dimethylamino-pyridine;
DIC: N,N'-diisopropylcarbodiimide;
TFA: trifluoroacetic acid;
DIEA: N,N-diisopropylethylamine;
DCM: dichloromethane;
TMOF: trimethylorthoformate;
HATU: azabenzotriazolyl-N,N,N',N'-tetramethyluronium hexafluorophosphate;
CDI: carbonyldiimidazole
NMP: N-methylpyrrolidinone
DMA: N,N-dimethyl acetamide
RT: room temperature
IPA: isopropyl alcohol MeOH: methanol
MeOEtOH: 2-methoxyethanol
DCE: 1,2-dichloroethane
THF: tetrahydrofuran
ACN: acetonitrile
Wang resin: p-benzyloxybenzyl alcohol-polystyrene
Br-Wang resin: p-benzyloxybenzyl bromide-polystyrene
PP: polypropylene
PPh3Br2: triphenylphosphine dibromide
DMAP: 4-dimethylamino-pyridine
KOtBu: potassium tert-butoxide
NaOMe: sodium methoxide
BtCH2CN: 1-(cyanomethyl)benzotriazole
DBU: 1,8-diazabicyclo[5.4.0]undec-7-ene
Boc: tertbutoxycarbonyl;
AcOH: acetic acid
HPLC/MS: high performance liquid chromatography—mass spectrometry;
FIA-MS: flow injection analysis—mass spectrometry
ELSD: evaporative light scattering detector
THB: Todd Hewitt Broth
OD: optical density

EXAMPLE 1

Preparation of N-Substituted 6-(4-benzoyl) piperazinonicotinamides

Example 1 describes 62 variations at the $R_7$ position, which is included as —C(O)—NH—$R_7$ at the $R_2$ position. The 62 variations were derived from 62 different primary amines, with piperazine the building block for the $R_5$ position and benzoic acid the building block for the $R_6$ position and X being —C(O)—.

Step 1: Chloro Displacement with Ri-primary Amines on Merrifield Resin.

Two porous polypropylene packets (Tea-bags, 60 mm×60 mm, 65 $\mu$), each containing 1.5 g of Merrifield resin (1.48 meq/g ), were heated in a solution of the appropriate Rl-primary amine (60 mmol) in N-methylpyrrolidinone (60 mL) at 90° C. for 16–24 hours. The packets were washed with DMF (6×60 mL) and MeOH (4×60 mL), then dried in air for 2 hours.

Step 2: Coupling 6-Chloronicotinic Acid to Resin Bound Amine.

The two packets were shaken with a solution of 6-Chloronicotinic acid (3.3g, 20 mmol), DIC (3.2g, 24 mmol), HOBt (2.7g, 20 mmol) and DMAP (0.28g, 2.4 mmol) in DMF (70 mL) for 24 hours. The packets were washed alternately with DMF (80 mL) and MeOH (80 mL) 3 cycles followed by MeOH (2×80 mL). The packets were then dried in air for 2 hours.

Step 3: Substitution of the Chloro Group with Piperazine.

The packets were heated in a solution of piperazine (6.0g, 70 mmol) in N-methylpyrrolidinone (70 mL) at 75° C. for 24 hours. The packets were washed with DMF (6×80 mL) and MeOH (4×80 mL), then dried in air for 2 hours.

Step 4: Coupling Benzoic Acid to Resin Bound Piperazine.

The packets were cut open and the resin was suspended in N-methylpyrrolidinone (40 mL). The suspension was distributed equally into 80 wells of a microtiter plate (2 mL×96). A solution containing 0.8 M benzoic acid and 0.30 M HOBt in N-methylpyrrolidinone was prepared, of which 300 $\mu$L was added to each well followed by the addition of DIC (56 $\mu$L, 0.36 mmol). The plate was tightly capped, shaken at ambient temperature for 24 hours. The resin was washed alternately with DMF (3×1 mL/well) and MeOH (2×1 mL/well) 5 cycles and MeOH (5×1 mL/well). The plate was dried in air for three days. The plate was treated with gaseous HF at room temperature for 4 hours. After complete removal of HF under a nitrogen stream followed by vacuum, the piate was extracted with ACOH (3×0.5 mL/well). The extractions were lyophilized to give the resulting compounds.

The 62 primary amines used were as follows:
1-(3-Aminopropyl)2-pyrrolidinone
2,4-Dichlorophenethylamine
1-(3-Aminopropyl)imidazole
Isopropylamine
4-Amino-1-benzylpiperidine
2-(2-Chlorophenyl)ethylamine
Cyclopropylamine
N-(2-Aminoethyl)-N-ethyl-m-toluidine
2-(3-Chlorophenyl)ethylamine
Histamine
2-(4-Chlorophenyl)ethylamine
1-Methyl-3-phenylpropylamine
2-Amino-5-diethylaminopentane
3,4-Dimethoxyphenethylamine
Tryptamine
Amylamine
3-Butoxypropylamine
Cyclopentylamine
Heptylamine
Ethyl 4-amino-1-piperidine carboxylate
Sec-Butylamine
2-Amino-1-methoxypropane
1,2-Dimethylpropylamine
2-Aminoheptahe
1,3-Dimethylbutylamine
2-Amino-5-methylhexane
2-Amino-1-methoxybutane
2-Aminooctane
Cyclobutylamine Hydrochloride
3-Aminopentane
3-(Di-N-Butylamino)propylamine
Butylamine
N-Octylamine
Isoamylamine
N,N-Dimethyl-1,3-propanediamine
N-(3-Aminopropyl)-N-Methylaniline
Tetrahydrofurfurylamine
3-Ethoxypropylamine
4-Phenylbutylamine
1-(2-Aminoethyl)pyrrolidine
4-(3-Aminopropyl)morpholine
1-(3-Aminopropyl)-2-pipecoline
2-(2-Aminoethyl)-1-methylpyrrolidine
3-Diethylaminopropylamine
3-(Methylthio)propylamine
1-(3-Aminopropyl)pyrrolidine
Cyclohexylamine
1-(2-Aminoethyl)piperidine
4-(2-Aminoethyl)morpholine
Phenethylamine 3-Phenyl-1-propylamine
Cycloheptylamine
1-(3-Aminopropyl)-4-methylpiperazine
4-Methylcyclohexylamine
2-(2-Aminoethyl)pyridine
Neopentylamine
2-(4-Methoxyphenyl)ethylamine
2-Methylcyclohexylamine
3-Methylcyclohexyl amine
Allylamine
2-(Aminomethyl)-1-ethyl-pyrrolidine
3-(Aminomethyl)pyridine

EXAMPLE 2

Preparation of N-phenethyl 6-substituted Nicotinamides

Using the same experimental procedures as described in Example 1, additional 6-aminonicotinamides were synthesized. Spectfically, two variations at the $R_5$ position (with piperazine and 1,4-diaminobutane the building blocks; phenethylamine the building block at the $R_7$ position, which is included as —C(O)—NH—$R_7$ at the $R_2$ position; 2-furoic acid the building block for the $R_6$ position and X being —C(O)—.

EXAMPLE 3

Preparation of N-cyclohexyl 6-Piperazinonicotinamides

Using the same experimental procedures as described in Example 1, additional 6-aminonicotinamides were synthesized. Specifically, 80 carboxylic acid variations were used for the $R_6$ position, with cyclohexylamine the building block at the $R_7$ position, which is included as —C(O)—NH—$R_7$ at the $R_2$ position; piperazine the building block at the $R_5$ position; and X being —C(O)—.

The 80 carboxylic acids used were as follows:

3-Methoxy-2-nitrobenzoic acid
3,5-Bis(trifluoromethyl)benzoic acid
5-Methoxy-2-nitrobenzoic acid
2-Methoxy-4-nitrobenzoic acid
4-(Trifluoromethoxy)benzoic acid
2,3,4,5-Tetrafluorobenzoic acid
N-Methylhippuric acid
Pentamethylbenzoic acid
Indazole-3-carboxylic acid
2,6-Dichloronicotinic acid
2,4-Dichlorobenzoic acid
2,5-Dichlorobenzoic acid
3,5-Dichlorobenzoic acid
Chromone-2-carboxylic acid
2-(Trifluoromethyl)cinnamic acid
4-Iodobenzoic acid
1-Methyl-3-indoleacetic acid
2-Chloro-6-fluorophenylacetic acid
1-Naphthylacetic acid
3,4-Difluorohydrocinnamic acid
4-Fluoro-3-nitrobenzoic acid
2-Bromo-5-methoxybenzoic acid
4-Chloro-alpha-methylphenylacetic acid
2,6-Dimethoxybenzoic acid
2-Methyl-3-nitrobenzoic acid
3-Methyl-4-nitrobenzoic acid
2-Nitrophenylacetic acid
2-Methyl-6-nitrobenzoic acid
5-Methyl-2-nitrobenzoic acid
3-Oxo-1-indancarboxylic acid
2-Pyrazinecarboxylic acid
1-Methylindole-3-carboxylic acid
1-Isoquinolinecarboxylic acid
1-Acetylpiperidine-4-carboxylic acid
2-(Carboxymethylthio)pyrimidine
2,2-Dichloro-1-methylcyclopropanecarboxylic acid
o-Nitrobenzoic acid
3-Cyanobenzoic acid
4-Methyl-1,2,3-thiadiazole-5-carboxylic acid
2,4,6-Trimethylbenzoic acid
2-Phenylbutyric acid
3-Methyl-2-thiophenecarboxylic acid
2,5-Dimethylphenylacetic acid
trans-2-Phenyl-1-cyclopropanecarboxylic acid
2-Chloronicotinic acid
Phenoxyacetic acid
2,4-Dimethylbenzoic acid
o-Tolylacetic acid
p-Tolylacetic acid
2-Bromobenzoic acid
Cyclohexylacetic acid
3-Methyl-2-thiophenecarboxylic acid
5-Methylthiophene-2-carboxylic acid
Thiophene-3-acetic acid
2-Methylpyrazine-5-carboxylic acid
2,2-Dimethylvaleric acid
Cyclohexanecarboxylic acid
Cyclohexanepropionic acid
3-Thiophenecarboxylic acid
5-Methylisoxazole-4-carboxylic acid
5-Methylisoxazole-3-carboxylic acid
2-Methyl-3-furoic acid
Picolinic acid
2-Ethylbutyric acid
tert-Butylacetic acid
3-Methylpentanoic acid
Levulinic acid
Tetrahydrofuran-2-carboxylic acid
Trifluoroacetic acid
2-Furoic acid
3-Furoic acid
Ethoxyacetic acid
Phthalide-3-acetic acid
Isovaleric acid
Pivalic acid
Valeric acid
Cyclopentyl acetic acid
Cyclobutanecarboxylic acid Methoxyacetic acid Propionic acid

EXAMPLE 4

Synthesis of a Library of 9,920 Different 6-Aminonicotinamides

Using the same experimental procedures as described in Example 1, a library of 9,920 6-aminonicotinamides was synthesized by using all possible combinations of the 62 primary amines, 2 diamines and 80 carboxylic acids (R3) listed above.

EXAMPLE 5

Melanocortin Receptor Assay

This example describes methods for assaying binding to MC receptors.

All cell culture media and reagents are obtained from GibcoBRL (Gaithersburg Md.), except for COSMIC CALF SERUM (HyClone; Logan Utah). HEK 293 cell lines are transfected with the human MC receptors hMCR-1, hMCR-3, and hMCR-4 (Gantz et al., *Biochem. Biophys. Res. Comm.* 200:1214–1220 (1994); Gantz et al., *J. Biol. Chem.* 268:8246–8250 (1993); Gantz et al. *J. Biol. Chem.* 268:15174–15179 (1993); Haskell-Leuvano et al., *Biochem. Biophys. Res. Comm.* 204:1137–1142 (1994); each of which is incorporated herein by reference). Vectors for construction of an hMCR-5 expressing cell line are obtained, and a line of HEK 293 cells expressing hMCR-5 are constructed (Gantz, supra, 1994). hMCR-5 has been described previously (Franberg et al., *Biochem. Bionhys. Res. Commun.* 236:489–492 (1997); Chowdhary et al., *Cytogenet. Cell Genet.* 68:1–2 (1995); Chowdhary et al., *Cytogenet. Cell Genet.* 68:79–81 (1995), each of which is incorporated herein by reference). HEK 293 cells are maintained in DMEM, 25 mM HEPES, 2 mM glutamine, non-essential amino acids, vitamins, sodium pyruvate, 10% COSMIC CALF SERUM, 100 units/ml penicillin, 100 µg/ml streptomycin and 0.2 mg/ml G418 to maintain selection.

Before assaying, cells are washed once with phosphate buffered saline ("PBS"; without $Ca^{2+}$ and $Mg^{2+}$), and stripped from the flasks using 0.25% trypsin and 0.5 mM EDTA. Cells are suspended in PBS, 10% COSMIC CALF SERUM and 1 mM $CaCl_2$. Cell suspensions are prepared at a density of $2\times10^4$ cells/ml for HEK 293 cells expressing hMCR-3, hMCR-4 or hMCR-5, and $1\times10^5$ cells/ml for HEK 293 cells expressing hMCR-1.Suspensions are placed in a water bath and allowed to warm to 37° C. for 1 hr.

Binding assays are performed in a total volume of 250 µl for HEK 293 cells. Control and test compounds are dissolved in distilled water. $^{125}$I-HP 467 (50,000 dpm) (2000 Ci/mmol) (custom labeled by Amersham; Arlington Heights Ill.) is prepared in 50 mM Tris, pH 7.4, 2 mg/ml BSA, 10 mM $CaCl_2$, 5 mM $MgCl_2$, 2 mM EDTA and added to each tube. To each tube is added $4\times10^3$ HEK 293 cells expressing hMCR-3, hMCR-4 or hMCR-5, or $2\times10^4$ cells expressing hMCR-1.Assays are incubated for 2.5 hr at 37° C.

GF/B filter plates are prepared by soaking for at least one hour in 5 mg/ml BSA and 10 mM $CaCl_2$. Assays are filtered using a Brandel 96-well cell harvester (Brandel Inc.; Gaithersburg, Md.). The filters are washed four times with cold 50 mM Tris, pH 7.4, the filter plates are dehydrated for 2 hr and 35 µl of MICROSCINT is added to each well. Filter plates are counted using a Packard Topqount (Packard Instrument Co.) and data analyzed using GraphPad PRISM v2.0 (GraphPad Software-Inc.; San Diego Calif.) and Microsoft EXCEL v5.0a (Microsoft Corp.; Redmond Wash.).

To assay pyridine carboxamide or sulfonamide derivative compounds, binding assays are performed in duplicate in a 96 well format. HP 467 was prepared in 50 mM Tris, pH 7.4, and $^{125}$I-HP 467 was diluted to give 100,000 dpm per 50 µl. A pyridine carboxamide or sulfonamide derivative compound, synthesized as described in Examples 1 to 4, is added to the well in 25 µl aliquots. A 25 µl aliquot of $^{125}$1-HP 467 is added to each well. A 0.2 ml aliquot of suspended cells is added to each well to give the cell numbers indicate above, and the cells are incubated at 37° C. for 2.5 hr. Cells are harvested on GF/B filter plates as described above and counted.

EXAMPLE 6

Anti-microbial Screen

Streptococcus pyogenes (ATCC# 97-03 14289) are grown in Todd Hewitt Broth (THB) (Difco Laboratories #0492-17-6) overnight until they reached an optical density of (OD= 0.636@ 570 nm) by reading 0.1 ml in a 96 well microtiter plate in a Molecular Devices Thermomax. This preparation is kept frozen as stocks in 30% v/v glycerol in 1.5 ml aliquots at −70° C. until used. Prior to screening, 1.5 ml aliquots are thawed and diluted into 50 ml THB. 200 ul of this dilution is added to 92 wells of microtiter plate. To three wells THB (200 ul) is added to serve as a blank and a sterility control. Test compounds in DMSO and appropriate concentrations of DMSO are added to Growth/Solvent Controls at 0 time. Plates are read at 0 time at 570 nm in the Molecular Devices plate reader to obtain compounds correction factors for insoluble or colored compounds. Plates are read again at 4 hrs.

Compounds are assayed at a concentration of 170 µg/ml. Percent inhibition for each compound is calculated using the following formulae:

Color correct=(O.D. 0 hr—Blank 0 hr)-(Solvent Control 0 hr—Blank 0 hr)

% Inhibition=100—(O.D. test compound 4 hr—Blank 4 hr—color correct) divided by (O.D. growth/solvent control 4 hr—Blank 4 hr)

EXAMPLE 7

Penile Erection due to Administration of a Pyridine Carboxamide or Sulfonamide Derivative Compound Adult male rats are housed 2–3 per cage and are acclimated to the standard vivarium light cycle (12 hr. light, 12 hr. dark), rat chow and water for a least a week prior to testing. All experiments are performed between 9 a.m. and noon and rats are placed in cylindrical, clear plexiglass chambers during the 60 minute observation period. Mirrors are positioned below and to the sides of the chambers, to improve viewing.

Observations begin 10 minutes after an unstraperitoneal injection of either saline or compound. An observer counts the number of grooming motions, stretches, yawns and penile erections (spontaneously occurring, not elicited by genital grooming) and records them every 5 minutes, for a total of 60 minutes. The observer is unaware of the treatment and animals are tested once, with n=6 in each group. Values in the figures represent the group mean and standard error of the mean. HP 228 can be used as a positive control for penile erections. Significant differences between groups are determined by an overall analysis of variance and the Student Neunmann-Keuls post hoc test can be used to identify individual differences between groups (p<0.05).

Although the invention has been described with reference to the examples provided above, it should be understood that various modifications can be made by those skilled in the art without departing from the invention. Accordingly, the invention is set out in the following claims.

We claim:

1. A combinatorial library of two or more compounds of the formula:

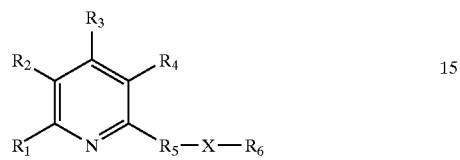

wherein:

X is selected from the group consisting of —C(O)— and —S(O$_2$)—;

one of $R_1$, $R_2$, $R_3$ and $R_4$ is the formula —X—N—$R_7R_8$, wherein X is a carbonyl group (—C(O)—) or a sulfonyl group (—S(O$_2$)—);

$R_7$ is selected from the group consisting of a hydrogen atom, $C_1$ to $C_{12}$ alkyl, $C_1$ to $C_{12}$ substituted alkyl, phenyl, substituted phenyl, heterocycle, substituted heterocycle, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, $C_2$ to $C_{12}$ alkenyl, $C_2$ to $C_{12}$ substituted alkenyl, $C_7$ to $C_{18}$ phlenylalkyl, $C_7$ to $C_{18}$ substituted phenylalkyl, $C_1$ to $C_{12}$ heterocycloalkyl and $C_1$ to $C_{12}$ substituted heterocycloalkyl; and $R_8$ is selected from the group consisting of a hydrogen atom, $C_1$ to $C_{12}$ alkyl, $C_1$ to $C_{12}$ substituted alkyl, non-aromatic heterocycle, non-aromatic substituted heterocycle, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, $C_2$ to $C_{12}$ alkenyl, $C_2$ to $C_{12}$ substituted alkenyl, $C_7$ to $C_{18}$ phenylalkyl, $C_7$ to $C_{18}$ substituted phenylalkyl, $C_1$ to $C_{12}$ heterocycloalkyl and $C_1$ to $C_{12}$ substituted heterocycloalkyl;

the remaining $R_1$, $R_2$, $R_3$ and $R_4$ are, independently, selected from the group consisting of a hydrogen atom, hydroxy, protected hydroxy, nitro, cyano, $C_1$ to $C_{12}$ alkyl, $C_2$ to $C_{12}$ alkenyl, $C_2$ to $C_{12}$ alkynyl, $C_1$ to $C_{12}$ substituted alkyl, $C_2$ to $C_{12}$ substituted alkenyl, $C_2$ to $C_{12}$ substituted alkynyl, $C_1$ to $C_{12}$ alkoxy, $C_1$ to $C_{12}$ substituted alkoxy, $C_1$ to $C_{12}$ acyloxy, $C_1$ to $C_{12}$ acyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, heterocyclic ring, substituted heterocyclic ring, $C_7$ to $C_{18}$ phenylalkyl, $C_7$ to $C_{18}$ suibstituted phenylalkyl, $C_1$ to $C_{12}$ heterocycloalkyl, $C_1$ to $C_{12}$ substituted heterocycloalkyl, phenyl, substituted phenyl, naphthyl, substituted naphthyl, cyclic $C_3$ to $C_7$ allkylene, substituted cyclic $C_3$ to $C_7$ alkylene, cyclic $C_2$ to $C_7$ heteroalkylene, substituted cyclic $C_2$ to $C_7$ heteroalkylene, carboxy, protected carboxy, hydroxymethyl, protected hydroxymethyl, protected amino, (monosubstituted)amino, protected (monosubstituted)amino, (disubstituted)amino, $C_1$ to $C_{12}$ alkylamino, $C_1$ to $C_{10}$ substituted alkylamino, carboxamide, protected carboxamide, $C_1$ to $C_{10}$ alkylthio, $C_1$ to $C_{10}$ substituted alkylthio, $C_1$ to $C_{10}$ alkylsulfonyl, $C_1$ to $C_{10}$ substituted alkylsulfonyl, $C_1$ to $C_{10}$ alkylsulfoxide, $C_1$ to $C_{10}$ substituted alkylsulfoxide, phenylthio, substituted phenylthio, phenylsulfoxide, substituted phenylsulfoxide, phenylsulfonyl and substituted phenylsulfonyl;

$R_5$ is the formula —DWE—, wherein
(i) D and E are each —NH— and W is selected from the group consisting of $C_2$ to $C_{12}$ alkylene, $C_2$ to $C_{12}$ alkenylene, $C_2$ to $C_{12}$ alkynylene, $C_2$ to $C_{12}$ substituted alkylene, $C_2$ to $C_{12}$ substituted alkenylene, $C_2$ to $C_{12}$ substituted alkynylene, $C_7$ to $C_{18}$ phenylalkylene, $C_7$ to $C_{18}$ substituted phenylalkylene, $C_1$ to $C_{12}$ heterocycloalkylene and $C_1$ to $C_{12}$ substituted heterocycloalkylene phenylene, substituted phenylene, $C_3$ to $C_7$ cycloalkylene, $C_3$ to $C_7$ substituted cycloalkylene, $C_5$ to $C_7$ cycloalkenylene, $C_5$ to $C_7$ substituted cycloalkenylene, heterocyclene and substituted heterocyclene; or
(ii) D, W and E together form a non-aromatic heterocyclene or substituted non-aromatic heterocyclene having at least two ring nitrogen atoms, one ring nitrogen atom directly attached to X—$R_6$ depicted in the above formula and the other ring nitrogen atom directly attached to the pyridine depicted in the above formula; and $R_6$ is selected from the group consisting of a hydrogen atom, $C_1$ to $C_{12}$ alkyl, $C_1$ to $C_{12}$ substituted alkyl, $C_2$ to $C_{12}$ alkenyl, $C_2$ to $C_{12}$ substituted alkenyl, phenyl, substituted phenyl, naphthyl, substituted naphthyl, $C_7$ to $C_{18}$ phenylalkyl, $C_7$ to $C_{18}$ substituted phenylalkyl, $C_1$ to $C_{12}$ heterocycloalkyl, $C_1$ to $C_{12}$ substituted heterocycloalkyl, heteroaryl, substituted heteroaryl, heterocycle and substituted heterocycle, wherein said heterocycle is a five-membered to eight-membered ring;

wherein $R_7$ or $R_8$ can be attached to a functionalized resin; or
a pharmaceutically acceptable salt of a compound thereof.

2. The combinatorial library of claim 1, wherein $R_7$ is not a hydrogen atom.

3. The combinatorial library of claim 1, wherein $R_8$ is a hydrogen atom.

4. The combinatorial library of claim 1, wherein X is —C(O)—.

5. The combinatorial library of claim 1, wherein:
$R_2$ is the formula —X—NH—$R_7$, wherein X is —C(O)— and $R_7$ is selected from the group consisting of $C_1$ to $C_{12}$ alkyl, $C_1$ to $C_{12}$ substituted alkyl, $C_3$ to $C_7$ cycloalkyl, $C_3$ to $C_7$ substituted cycloalkyl, $C_7$ to $C_{18}$ phenylalkyl, $C_7$ to $C_{18}$ substituted phenylalkyl, $C_1$ to $C_{12}$ heterocycloalkyl and $C_1$ to $C_{12}$ substituted heterocycloalkyl.

6. The combinatorial library of claim 1, wherein $R_1$, $R_3$ and $R_4$ are each a hydrogen atom.

7. The combinatorial library of claim 1, wherein $R_5$ is the formula —DWE—, wherein
(i) D and E are each —NH— and W is selected from the group consisting of $C_2$ to $C_{12}$ alkylene and $C_2$ to $C_{12}$ substituted alkylene; or
(ii) D, W and E together form a non-aromatic heterocyclene or substituted non-aromatic heterocyclene having at least two ring nitrogen atoms, one ring nitrogen atom directly attached to X—$R_6$ depicted in the above formula and the other ring nitrogen atom directly attached to the pyridine depicted in the above formula.

8. The combinatorial library of claim 1, wherein $R_6$ is selected from the group consisting of $C_1$ to $C_{12}$ alkyl, $C_1$ to $C_{12}$ substituted alkyl, $C_2$ to $C_{12}$ alkenyl, $C_2$ to $C_{12}$ substituted alkenyl, phenyl, substituted phenyl, $C_7$ to $C_{18}$ phenylalkyl, $C_7$ to $C_{18}$ substituted phenylalkyl, $C_1$ to $C_{12}$ heterocycloalkyl, $C_1$ to $C_{12}$ substituted heterocycloalkyl, heteroaryl, substituted heteroaryl, heterocycle and substituted heterocycle.

9. The combinatorial library of claim 1, wherein X is —C(O)—;

$R_2$ is the formula —X—NH—$R_7$, wherein X is —C(O)— and $R_7$ is selected from the group consisting of $C_1$ to $C_{12}$ alkyl, $C_1$ to $C_{12}$ substituted alkyl, $C_3$ to $C_7$ cycloalkyl, $C_3$ to $C_7$ substituted cycloalkyl, $C_7$ to $C_{18}$ phenylalkyl, $C_7$ to $C_{18}$ substituted phenylalkyl, $C_1$ to $C_{12}$ heterocycloalkyl and $C_1$ to $C_{12}$ substituted heterocycloalkyl;

$R_1$, $R_3$ and $R_4$ are each a hydrogen atom;

$R_5$ is the formula —DWE—, wherein
(i) D and E are each —NH— and W is selected from the group consisting of $C_2$ to $C_{12}$ alkylene and $C_2$ to $C_{12}$ substituted alkylene; or
(ii) D, W and E together form a non-aromatic heterocyclene or substituted non-aromatic heterocyclene having at least two ring nitrogen atoms, one ring nitrogen atom directly attached to X—$R_6$ depicted in the above formula and the other ring nitrogen atom directly attached to the pyridine depicted in the above formula; and $R_6$ is selected from the group consisting of $C_1$ to $C_{12}$ alkyl, $C_1$ to $C_{12}$ substituted alkyl, $C_2$ to $C_{12}$ alkenyl, $C_2$ to $C_{12}$ substituted alkenyl, phenyl, substituted phenyl, $C_7$ to $C_{18}$ phenylalkyl, $C_7$ to $C_{18}$ substituted phenylalkyl, $C_1$ to $C_{12}$ heterocycloalkyl, $C_1$ to $C_{12}$ substituted heterocycloalkyl, heteroaryl, substituted heteroaryl, heterocycle and substituted heterocycle.

10. The combinatorial library of claim 1, wherein X is —C(O)—;

$R_2$ is the formula —X—NH—$R_7$, wherein X is —C(O)— and $R_7$ is selected from the group consisting of 3-(2-oxo-1-pyrrolidino) propyl, 2,4-dichlorophenethyl, 3-(1-imidazolyl)propyl, isopropyl, 1-benzyl-4-piperidinyl, 2-(2-chlorophenyl)ethyl, cyclopropyl, 2-(N-(3-methylphenyl)ethylamino)ethyl, 2-(3-chlorophenyl)ethyl, 2-(4-imidazolyl)ethyl, 2-(4-chlorophenyl)ethyl, 1-methyl-3-phenylpropyl, 2-(5-diethylamino)pentyl, 3,4-dimethoxyphenethyl, 2 (3-indolyl)cthyl, amyl, 3-butoxypropyl, cyclopentyl, heptyl, 1-ethoxycarbonyl-4-piperidinyl, sec-butyl, 1-methoxy-2-propyl, 3-methyl-2-butyl, 2-heptyl, 4-methyl-2-pentyl, 5-methyl-2-hexyl, 1-methoxy-2-butyl, 2-octyl, cyclobutyl, 3-pentyl, 3-(di-N-butylamino)propyl, butyl, n-octyl, isoamyl, 3-(N,N-dimethylamino)propyl, 3-(N-methylanilino) aminopropyl, tetrahydrofurturyl, 3-ethoxypropyl, 4-phenylbutyl, 2-(1-pyrrolidino)ethyl, 3-(4-morpholino)propyl, 3-(2-methylpiperidino)propyl, 2-(1-methylpyrrolidin-2-yl)ethyl, 3-(diethylamino) propyl, 3-(methylthio)propyl, 3-(1-pyrrolidino)propyl, cyclohexyl, 2-(1-piperidino) ethyl, 2-(4-morpholino) ethyl, phenethyl, 3-phenylpropyl, cycloheptyl, 3-(4-methylpiperazin-1-yl)propyl, 4-methylcyclohexyl, 2-(2-pyridinyl) ethyl, neopentyl, 2-(4-methoxyphenyl) ethyl, 2-methylcyclohexyl, 3-methylcyclohexyl, allyl, (1-ethylpyrrolidin-2-yl))methyl and (3-pyridinyl) methyl;

$R_1$, $R_3$ and $R_4$ are each a hydrogen atom;

$R_5$ is selected from the group consisting of 1,4-diaminobutylene and 1,4-piperazylene; and $R_6$ is selected from the group consisting of 3-methoxy-2-nitrophenyl, 3,5-bis(trifluoromethyl)phenyl, 5-methoxy-2-nitrophenyl, 2-methoxy-4-nitrophenyl, 4-(trifluoromethoxy)phenyl, 2,3,4,5-tetrafluorophenyl, (N-methylbenzamido)methyl, pentamethylphenyl, 3-indazolyl, 2,6-dichloro-3-pyridinyl, 2,4-dichlorophenyl, 2,5-dichlorophenyl, 3,5-dichlorophenyl, 2-chroinoiyl, 2-(trifluoromethyl)styryl, 4-iodophenyl, (1 methylindo-3-yl)methyl, 2-chloro-6-fluorobenzyl, (1-naphthyl)methyl, 3,4-difluorophenethyl, 4-fluoro-3-nitrophenyl, 2-bromo-5-methoxyphenyl, 4-chloro-α-methylphenethyl, 2,6-dimethoxyphenyl, 2-methyl-3-nitrophenyl, 3-methyl-4-nitrophenyl, 2-nitrophenethyl, 2-methyl-6-nitrophenyl, 5-methyl-2-nitrophenyl, 3-oxo-1-indanyl, 2-pyrazinyl, 1-methylindol-3-yl, 1-isoquinolinyl, 1-acetylpiperidin-4-yl, pyrimidin-2-ylthiomethyl, 2,2-dichloro-1-methylcyclopropyl, o-nitrophenyl, 3-cyanophenyl, 4-methyl-1,2,3-thiadiazol-5-yl, 2,4,6-trimethylphenyl, 2-(phenyl)propyl, 3-methyl-2-thienyl, 2,5-,dimethylbenzyl, trans-2-phenyl-1-cyclopropyl, 2-chloro-3-pyridinyl, phenoxymethyl, 2,4-dimethylphenyl, o-methylbenzyl, p-methylbenzyl, 2-bromophenyl, cyclohexylmethyl, 3-methylthien-2-yl, 5-methylthien-2-yl, (3-thienyl)methyl, 2-methylpyrazin-5-yl, 2-methyl-2-pentyl, cyclohexyl, 3-cyclohexylpropyl, 3-thienyl, 5-methylisoxazol-4-yl, 5-methylisoxazol-3-yl, 2-methyl-3-furyl, 2-pyridinyl, 3-pentyl, 1-(2,2-dimethyl)propyl, 1-(2-methyl)butyl, 2-acetylethyl, 2-tetrahydrofuryl, trifluoromethyl, 2-furyl, 3-furyl, ethoxymethyl, 3-phthalidylmethyl, sec-butyl, tert-butyl, 1-butyl, cyclopentylmethyl, cyclobutyl, methoxymethyl and ethyl.

11. A single compound of the formula:

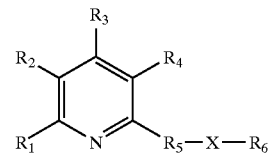

wherein:

X is selected from the group consisting of —C(O)— and —S(O$_2$)—;

one of $R_1$, $R_2$, $R_3$ and $R_4$ is the formula —X—N—$R_7R_8$, wherein X is a carbonyl group (—C(O)—) or a sulfonyl group (—S(O$_2$)—);

$R_7$ is selected from the group consisting of a hydrogen atom, $C_1$ to $C_{12}$ alkyl, $C_1$ to $C_{12}$ substituted alkyl, phenyl, substituted phenyl, heterocycle, substituted heterocycle, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, $C_2$ to $C_{12}$ alkenyl, $C_2$ to $C_{12}$ substituted alkenyl, $C_7$ to $C_{18}$ phenylalkyl, $C_7$ to $C_{18}$ substituted phenylalkyl, $C_1$ to $C_{12}$ heterocycloalkyl and $C_1$ to $C_{12}$ substituted heterocycloalkyl; and $R_8$ is selected from the group consisting of a hydrogen atom, $C_1$ to $C_{12}$ alkyl, $C_1$ to $C_{12}$ substituted alkyl, non-aromatic heterocycle, non-aromatic substituted heterocycle, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, $C_2$ to $C_{12}$ alkenyl, $C_2$ to $C_{12}$ substituted alkenyl, $C_7$ to $C_{18}$ phenylalkyl, $C_7$ to $C_{18}$ substituted phenylalkyl, $C_1$ to $C_{12}$ heterocycloalkyl and $C_1$ to $C_{12}$ substituted heterocycloalkyl;

the remaining $R_1$, $R_2$, $R_3$ and $R_4$ are, independently, selected from the group consisting of a hydrogen atom, hydroxy, protected hydroxy, nitro, cyano, $C_1$ to $C_{12}$ alkyl, $C_2$ to $C_{12}$ alkenyl, $C_2$ to $C_{12}$ alkynyl, $C_1$ to $C_{12}$ substituted alkyl, $C_2$ to $C_{12}$ substituted alkenyl, $C_2$ to $C_{12}$ substituted alkynyl, $C_1$ to $C_{12}$ alkoxy, $C_1$ to $C_{12}$ substituted alkoxy, $C_1$ to $C_{12}$ acyloxy, $C_1$ to $C_{12}$ acyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, heterocyclic ring, substituted heterocyclic ring, $C_7$ to $C_{18}$ phenylalkyl, $C_7$ to $C_{18}$ substituted phenylalkyl, $C_1$ to $C_{12}$ heterocycloalkyl, $C_1$ to $C_{12}$ substituted heterocycloalkyl, phenyl, substituted phenyl, naphthyl, substituted naphthyl, cyclic $C_3$ to $C_7$ alkylene, substituted cyclic $C_3$ to $C_7$ alkylene, cyclic $C_2$ to $C_7$ heteroalkylene, substituted cyclic $C_2$ to $C_7$ heteroalkylene, carboxy, protected carboxy, hydroxymethyl, protected hydroxymethyl, protected amino, (monosubstituted)amino, protected (monosubstituted)amino, (disubstituted)amino, $C_1$ to $C_{10}$ alkylamino, $C_1$ to $C_{10}$ substituted alkylamino, carboxamide, protected carboxamide, $C_1$ to $C_{10}$ alkylthio, $C_1$ to $C_{10}$ substituted alkylthio, $C_1$ to $C_{10}$ alkylsulfonyl, $C_1$ to $C_{10}$ substituted alkylsulfonyl, $C_1$ to $C_{10}$ alkylsulfoxide, $C_1$ to $C_{10}$ substituted alkylsulfoxide, phenylthio, substituted phenylthio, phenylsulfoxide, substituted phenylsulfoxide, phenylsulfonyl and substituted phenylsulfonyl;

$R_5$ is the formula —DWE—, wherein
  (i) D and E are each —NH— and W is selected from the group consisting of $C_2$ to $C_{12}$ alkylene, $C_2$ to $C_{12}$ alkenylene, $C_2$ to $C_{12}$ alkynylene, $C_2$ to $C_{12}$ substituted alkylene, $C_2$ to $C_{12}$ substituted alkenylene, $C_2$ to $C_{12}$ substituted alkynylene, $C_7$ to $C_{18}$ phenylalkylene, $C_7$ to $C_{18}$ substituted phenylalkylene, $C_1$ to $C_{12}$ heterocycloalkylene and $C_1$ to $C_{12}$ substituted heterocycloalkylene phenylene, substituted phenylene, $C_3$ to $C_7$ cycloalkylene, $C_3$ to $C_7$ substituted cycloalkylene, $C_5$ to $C_7$ cycloalkenylene, $C_5$ to $C_7$ substituted cycloalkenylene, heterocyclene and substituted heterocyclene; or
  (ii) D, W and E together form a non-aromatic heterocyclene or substituted non-aromatic heterocyclene having at least two ring nitrogen atoms, one ring nitrogen atom directly attached to X—$R_6$ depicted in the above formula and the other ring nitrogen atom directly attached to the pyridine depicted in the above formula; and $R_6$ is selected from the group consisting of a hydrogen atom, $C_1$ to $C_{12}$ alkyl, $C_1$ to $C_{12}$ substituted alkyl, $C_2$ to $C_{12}$ alkenyl, $C_2$ to $C_{12}$ substituted alkenyl, phenyl, substituted phenyl, naphthyl, substituted naphthyl, $C_7$ to $C_{18}$ phenylalkyl, $C_7$ to $C_{18}$ substituted phenylalkyl, $C_1$ to $C_{12}$ heterocycloalkyl, $C_1$ to $C_{12}$ substituted heterocycloalkyl, heteroaryl, substituted heteroaryl, heterocycle and substituted heterocycle, wherein said heterocycle is a five-membered to eight-membered ring; or a pharmaceutically acceptable salt of a compound thereof.

12. The single compound of claim 11, wherein $R_7$ is not a hydrogen atom.

13. The single compound of claim 11, wherein $R_8$ is a hydrogen atom.

14. The single compound of claim 11, wherein X is —C(O)—.

15. The single compound of claim 11, wherein:
$R_2$ is the formula —X—NH—$R_7$, wherein X is —C(O)— and $R_7$ is selected from the group consisting of $C_1$ to $C_2$ alkyl, $C_1$ to $C_{12}$ substituted alkyl, $C_3$ to $C_7$ cycloalkyl, $C_3$ to $C_7$ substituted cycloalkyl, $C_7$ to $C_{18}$ phenylalkyl, $C_7$ to $C_{18}$ substituted phenylalkyl, $C_1$ to $C_{12}$ heterocycloalkyl and $C_1$ to $C_{12}$ substituted heterocycloalkyl.

16. The single compound of claim 11, wherein $R_1$, $R_3$ and $R_4$ are each a hydrogen atom.

17. The single compound of claim 11, wherein $R_5$ is the formula —DWE—, wherein
  (i) D and E are each —NH— and W is selected from the group consisting of $C_2$ to $C_{12}$ alkylene and $C_2$ to $C_{12}$ substituted alkylene; or
  (ii) D, W and E together form a non-aromatic heterocyclene or substituted non-aromatic heterocyclene having at least two ring nitrogen atoms, one ring nitrogen atom directly attached to X—$R_6$ depicted in the above formula and the other ring nitrogen atom directly attached to the pyridine depicted in the above formula.

18. The single compound of claim 11, wherein
$R_6$ is selected from the group consisting of $C_1$ to $C_{12}$ alkyl, $C_1$ to $C_{12}$ substituted alkyl, $C_2$ to $C_{12}$ alkenyl, $C_2$ to $C_{12}$ substituted alkenyl, phenyl, substituted phenyl, $C_7$ to $C_{18}$ phenylalkyl, $C_7$ to $C_{18}$ substituted phenylalkyl, $C_1$ to $C_{12}$ heterocycloalkyl, $C_1$ to $C_{12}$ substituted heterocycloalkyl, heteroaryl, substituted heteroaryl, heterocycle and substituted heterocycle.

19. The single compound of claim 11, wherein X is —C(O)—;
$R_2$ is the formula —X—NH—$R_7$, wherein X is —C(O)— and $R_7$ is selected from the group consisting of $C_1$ to $C_{12}$ alkyl, $C_1$ to $C_{12}$ substituted alkyl, $C_3$ to $C_7$ cycloalkyl, $C_3$ to $C_7$ substituted cycloalkyl, $C_7$ to $C_{18}$ phenylalkyl, $C_7$ to $C_{18}$ substituted phenylalkyl, $C_1$ to $C_{12}$ heterocycloalkyl and $C_1$ to $C_{12}$ substituted heterocycloalkyl;

$R_1$, $R_3$ and $R_4$ are each a hydrogen atom;
$R_5$ is the formula —DWE—, wherein
  (i) D and E are each —NH— and W is selected from the group consisting of $C_2$ to $C_{12}$ alkylene and $C_2$ to $C_{12}$ substituted alkylene; or
  (ii) D, W and E together form a non-aromatic heterocyclene or substituted non-aromatic heterocyclene having at least two ring nitrogen atoms, one ring nitrogen atom directly attached to X—$R_6$ depicted in the above formula and the other ring nitrogen atom directly attached to the pyridine depicted in the above formula; and $R_6$ is selected from the group consisting of $C_1$ to $C_{12}$ alkyl, $C_1$ to $C_{12}$ substituted alkyl, $C_2$ to $C_{12}$ alkenyl, $C_2$ to $C_{12}$ substituted alkenyl, phenyl, substituted phenyl, $C_7$ to $C_{18}$ phenylalkyl, $C_7$ to $C_{18}$ substituted phenylalkyl, $C_1$ to $C_{12}$ heterocycloalkyl, $C_1$ to $C_{12}$ substituted heterocycloalkyl, heteroaryl, substituted heteroaryl, heterocycle and substituted heterocycle.

20. The single compound of claim 11, wherein X is —C(O)—;
$R_2$ is the formula —X—NH—$R_7$, wherein X is —C(O)— and $R_7$ is selected from the group consisting of 3-(2-oxo-1-pyrrolidino)propyl, 2,4-dichlorophenethyl, 3-(1-imidazolyl)propyl, isopropyl, 1-benzyl-4-piperidinyl, 2-(2-chlorophenyl)ethyl, cyclopropyl, 2-(N-(3-methylphenyl)ethylamino)ethyl, 2-(3-chlorophenyl)

ethyl, 2-(4-imidazolyl)ethyl, 2-(4-chlorophenyl)ethyl, 1-methyl-3-phenylpropyl, 2-(5-diethylamino)pentyl, 3,4-dimethoxyphenethyl, 2-(3-indolyl)ethyl, amyl, 3 butoxypropyl, cyclopentyl, heptyl, 1-ethoxycarbonyl-4-piperidinyl, sec-butyl, 1-methoxy-2-propyl, 3-methyl-2-butyl, 2-heptyl, 4-methyl-2-pentyl, 5-methyl-2-hexyl, 1-methoxy-2-butyl, 2-octyl, cyclobutyl, 3-pentyl, 3-(di-N-butylamino)propyl, butyl, n-octyl, isoamyl, 3-(N,N-dimethylamino)propyl, 3-(N-methylanilino)aminopropyl, tetrahydrofurfuryl, 3-ethoxypropyl, 4-phenylbutyl, 2-(1-pyrrolidino)ethyl, 3-(4-morpholino)propyl, 3-(2-methylpiperidino) propyl, 2-(1-methylpyrrolidin-2-yl)ethyl, 3-(diethylamino)propyl, 3-(methylthio)propyl, 3-(1-pyrrolidino)propyl, cyclohexyl, 2-(1-piperidino)ethyl, 2-(4-morpholino)ethyl, phenethyl, 3-phenylpropyl, cycloheptyl, 3-(4-methylpiperazin-1-yl)propyl, 4-methylcyclohexyl, 2-(2-pyridinyl)ethyl, neopentyl, 2-(4-methoxyphenyl)ethyl, 2-methylcyclohexyl, 3-methylcyclohexyl, allyl, (1-ethylpyrrolidin-2-yl)) methyl and (3-pyridinyl)methyl;

$R_1$, $R_3$ and $R_4$ are each a hydrogen atom;

$R_5$ is selected from the group consisting of 1,4-diaminobutylene and 1,4-piperazylene; and $R_6$ is selected from the group consisting of 3-methoxy-2-nitrophenyl, 3,5-bis(trifluoromethyl)phenyl, 5-methoxy-2-nitrophenyl, 2-methoxy-4-nitrophenyl, 4-(trifluoromethoxy)phenyl, 2,3,4,5-tetrafluorophenyl, (N-methylbenzamido)methyl, pentamethylphenyl, 3-indazolyl, 2,6-dichloro-3-pyridinyl, 2,4-dichlorophenyl, 2,5-dichlorophenyl, 3,5-dichlorophenyl, 2-chromonyl, 2-(trifluoromethyl) styryl, 4-iodophenyl, (1-methylindo-3-yl)methyl, 2-chloro-6-fluorobenzyl, (1-naphthyl)methyl, 3,4-difluorophenethyl, 4-fluoro-3-nitrophenyl, 2-bromo-5-methoxyphenyl, 4-chloro-α-methylphenethyl, 2,6-dimethoxyphenyl, 2-methyl-3-nitrophenyl, 3-methyl-4-nitrophenyl, 2-nitrophenethyl, 2-methyl-6-nitrophenyl, 5-methyl-2-nitrophenyl, 3-oxo-1-indanyl, 2-pyrazinyl, 1-methylindol-3-yl, 1-isoquinolinyl, 1-acetylpiperidin-4-yl, pyrimidin-2-ylthiomethyl, 2,2-dichloro1-methylcyclopropyl, o-nitrophenyl, 3-cyanophenyl, 4-methyl-1,2,3-thiadiazol-5-yl, 2,4,6-trimethylphenyl, 2-(phenyl)propyl, 3-methyl-2-thienyl, 2,5-dimethylbenzyl, trans-2-phenyl-1-cyclopropyl, 2-chloro-3-pyridinyl, phenoxymethyl, 2,4-dimethylphenyl, o-methylbenzyl, p-methylbenzyl, 2-bromophenyl, cyclohexylmethyl, 3-methylthien-2-yl, 5-methylthien-2-yl, (3-thienyl)methyl, 2-methylpyrazin-5-yl, 2-methyl-2-pentyl, cyclohexyl, 3-cyclohexylpropyl, 3-thienyl, 5-methylisoxazol-4-yl, 5-methylisoxazol-3-yl, 2-methyl-3-turyl, 2-pyridinyl, 3-pentyl, 1-(2,2-dimethyl)propyl, 1-(2-methyl)butyl, 2-acetylethyl, 2-tetrahydrofuryl, trifluoromethyl, 2-furyl, 3-furyl, ethoxymethyl, 3-phthalidylmethyl, sec-butyl, tert-butyl, 1-butyl, cyclopentylmethyl, cyclobutyl, methoxymethyl and ethyl.

21. A method of preparing the single compound of claim 11 comprising:

(a) reacting an amine containing the group variable-NH— with a pyridine that is substituted with a halo at the 6 position and is also substituted with a carboxy or sulfonyl group at one of the other positions of the pyridine ring, resulting in a pyridine that is substituted with a halo at the 6 position and is also substituted with a substituted carboxamide or sulfonamide containing, respectively, the group —C(O)—N(variable)- or the group —S(O$_2$)—N(variable)- at one of the other positions, wherein, respectively, the carboxamide carbon or the sulfur atom is directly attached to the pyridine ring; and (b) displacing the halo of the pyridine resulting from step (a) with (i) a diamine of the formula amino-variable-amino; (ii) an amino compound attached to a non-aromatic heterocycle or substituted heterocycle having at least one ring nitrogen atom; (iii) a non-aromatic heterocycle or substituted heterocycle having at least two ring nitrogen atoms; or (iv) a bicyclic non-aromatic heterocycle or substituted heterocycle, wherein each non-aromatic heterocycle or substituted heterocycle has at least one ring nitrogen atom.

22. The method of claim 21, wherein the terminal amino or imino group of the substituted pyridine resulting from step (b) is reacted with a carboxylic acid of the formula variable—COOH.

23. The method of claim 22, wherein the amine is attached to solid support before undergoing step (a).

24. The method of claim 22, wherein the pyridine is substituted with a carboxamide group at the 3 position before undergoing step (a).

* * * * *